US008314090B2

(12) United States Patent
Howbert et al.

(10) Patent No.: US 8,314,090 B2
(45) Date of Patent: Nov. 20, 2012

(54) METHODS OF SYNTHESIS OF BENZAZEPINE DERIVATIVES

(75) Inventors: J. Jeffry Howbert, Bellevue, WA (US); Venkat Reddy Kusukuntla, Germantown, WI (US); Alexander Tretyakov, Grafton, WI (US); Nathan Nielsen, Toronto (CA); Pavel Krasik, Aurora (CA); Ji-Long Jiang, Toronto (CA); Hong Woon Yang, Superior, CO (US)

(73) Assignees: VentiRx Pharmaceuticals, Inc., Seattle, WA (US); Array BioPharma, Inc., Boulder, CO (US)

( * ) Notice: Subject to any disclaimer, the term of this patent is extended or adjusted under 35 U.S.C. 154(b) by 230 days.

(21) Appl. No.: 12/614,048

(22) Filed: Nov. 6, 2009

(65) Prior Publication Data
US 2010/0216989 A1    Aug. 26, 2010

Related U.S. Application Data

(60) Provisional application No. 61/112,081, filed on Nov. 6, 2008.

(51) Int. Cl.
*A61P 31/00* (2006.01)
*A61K 31/55* (2006.01)
*C07D 223/16* (2006.01)

(52) U.S. Cl. .................. 514/213.01; 540/593
(58) Field of Classification Search ............ 514/213.01; 540/593
See application file for complete search history.

(56) References Cited

U.S. PATENT DOCUMENTS

| 6,043,238 | A  | 3/2000 | Cooper et al. |
| 7,691,877 | B2 | 4/2010 | Jones et al.  |
| 7,718,695 | B2 | 5/2010 | Kim et al.    |
| 2007/0197478 | A1 | 8/2007 | Jones et al. |
| 2008/0008682 | A1 | 1/2008 | Chong et al. |
| 2008/0057074 | A1 | 3/2008 | Takaoka et al. |
| 2008/0234251 | A1 | 9/2008 | Doherty et al. |
| 2010/0029585 | A1 | 2/2010 | Howbert et al. |
| 2011/0092485 | A1 | 4/2011 | Howbert et al. |
| 2011/0118235 | A1 | 5/2011 | Howbert et al. |

FOREIGN PATENT DOCUMENTS

| EP | 0825186     | 2/1998 |
| EP | 0825186 A1  | 2/1998 |
| WO | WO-03007955 A2 | 1/2003 |
| WO | WO-2005009973 A1 | 2/2005 |
| WO | WO-2005035534 A1 | 4/2005 |
| WO | WO-2007024612 A2 | 3/2007 |
| WO | WO-2007040840 A2 | 4/2007 |
| WO | WO-2007096151 A2 | 8/2007 |
| WO | WO-2007128460 A1 | 11/2007 |
| WO | WO-2008024892 A2 | 2/2008 |
| WO | WO-2008109177 A2 | 9/2008 |
| WO | WO-2008109180 A2 | 9/2008 |
| WO | WO-2008109181 A2 | 9/2008 |

OTHER PUBLICATIONS

Galaffu et al. "Highly Functionalised Sulfur-Based Silica Scavengers for the Efficient Removal of Palladium Species from Active Pharmaceutical Ingredients", *Organic Process Research & Development*, 11:406-413 2007.
Miyaura et al. "Palladium-Catalyzed Cross-Coupling Reactions of Organoboron Compounds," *Chem. Rev.*, 95:2457-2483 (1995).
Sigma-Aldrich and Reaxa Ltd. "Encapsulated Catalysts and Metal Scavengers", ChemFiles, Supplement 1 (2007).
Suzuki "Recent Advances in the Cross-Coupling Reactions of Organoboron Derivatives with Organic Electrophiles, 1995-1998," *J. Organomet. Chem.*, 576:147-168 (1999).

*Primary Examiner* — Brenda Coleman
(74) *Attorney, Agent, or Firm* — Mintz Levin Cohn Ferris Glovsky and Popeo, P.C.; Ivor R. Elrifi; Heidi A. Erlacher

(57) ABSTRACT

The disclosure describes method of synthesis of substituted benzazepine derivatives. Preferred methods according to the disclosure allow for large-scale preparation of benzazepine compounds having low levels of metal impurities. In some embodiments, preferred methods according to the disclosure also allow for the preparation of benzazepine derivatives without the use of chromatographic purification methods and in better yield than previously used methods for preparing such compounds. The methods disclosed herein find utility in synthetic organic chemistry as well as medicinal chemistry.

25 Claims, 1 Drawing Sheet

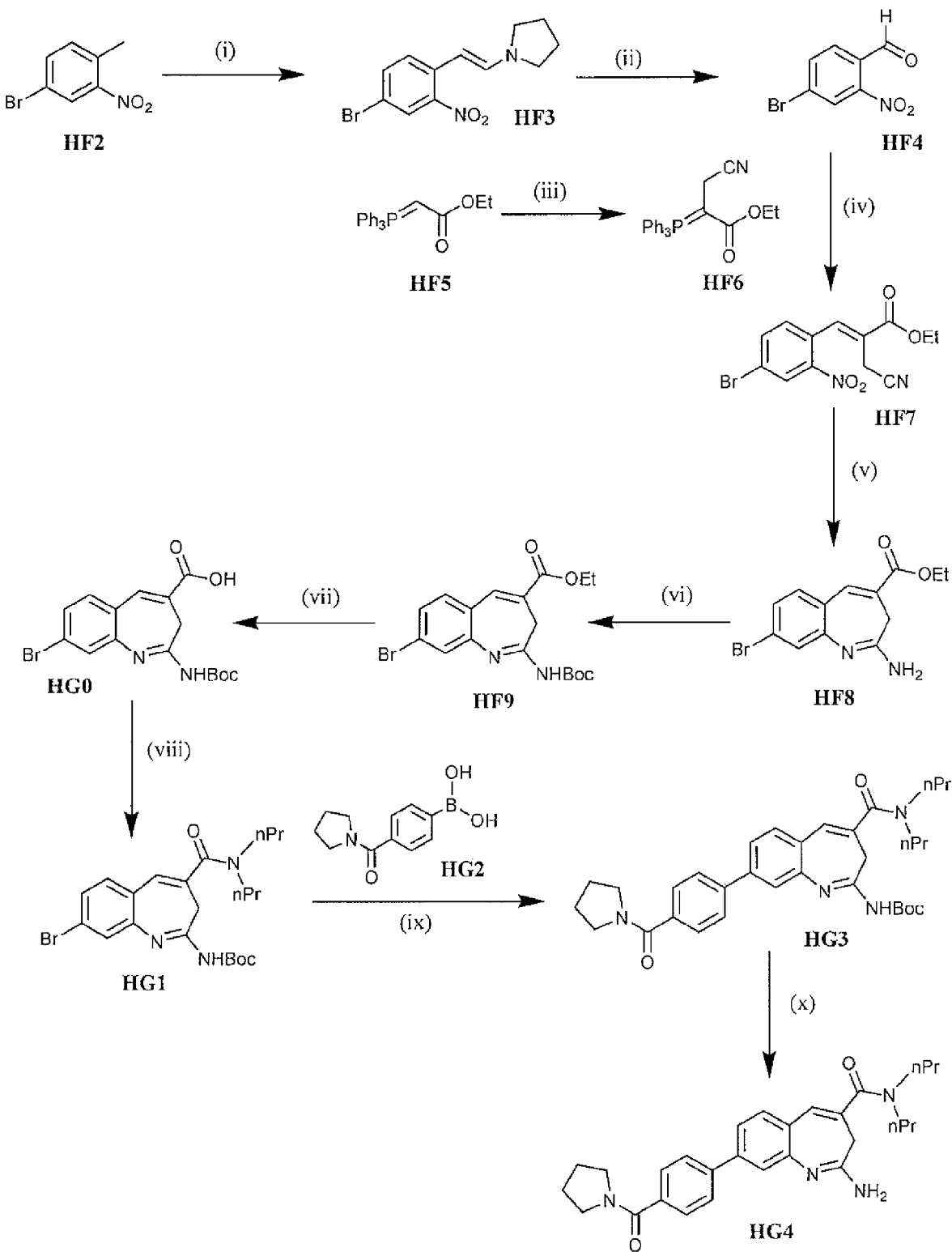

METHODS OF SYNTHESIS OF BENZAZEPINE DERIVATIVES

CROSS-REFERENCE TO RELATED APPLICATIONS

This application claims priority under 35 U.S.C. §119(e) to U.S. Provisional Application Ser. No. 61/112,081, filed Nov. 6, 2008, the disclosure of which is incorporated herein by reference.

TECHNICAL FIELD

This disclosure relates generally to methods suitable for synthesizing substituted benzazepine compounds. The invention finds utility, for example, in the fields of synthetic organic chemistry and pharmaceutical science.

BACKGROUND

The search for immunomodulator compounds and compositions has received much attention in recent years as the mechanisms by which the immune system produces protective or adverse physiological responses becomes more well known. The biological pathways involved in stimulation of the immune system, including stimulation of either or both innate immunity and adaptive immunity, are complex and allow numerous opportunities for the development of therapeutic treatments. For example, with the recent discovery of a family of receptor proteins known as Toll-like receptors (TLRs) believed to be involved in innate immunity as receptors for pathogen-associated molecular patterns (PAMPs), development of compounds suitable for therapeutic modulation of such receptors has gained in interest. A description of TLRs and their function in the immune response can be found in WO 2007/024612. Modulators of TLRs are potentially suitable as therapeutic agents for the treatment of, for example, conditions involving autoimmunity, inflammation, allergy, asthma, graft rejection, graft versus host disease (GvHD), infection, cancer, and immunodeficiency.

Substituted benzazepine derivatives are a class of compounds that have been targeted as immune stimulants. In particular, 2-amino-4-carboxylate derivatives of benzazepines have been recognized for their ability to modulate TLRs and otherwise provide desirable immunotherapeutic responses.

EP 0 825 186 A1 describes preparation of 2-aminobenzazepine derivatives. The compounds are described as useful in the treatment of immunosuppression, for example by stimulating the production of Granulocytes and Granulocyte-Macrophage Colony Stimulation Factor. 2-aminobenzazepine derivatives are described having a variety of substituents including annulated rings, functional groups, and the like. The reference also describes the use of such compounds in the treatment of myelosuppression.

WO 2007/024612 describes preparation of 8-substituted benzazepines as TLR modulators. A procedure is disclosed for preparing (1E,4E)-ethyl-2-amino-8-(4-(pyrrolidine-1-carbonyl)phenyl)-3H-benzo[b]azepine-4-carboxylate. The procedure involves seven steps, including as the penultimate step the palladium-catalyzed cross-coupling reaction between (1E,4E)-ethyl-8-bromo-2-(tert-butoxycarbonylamino)-3H-benzo[b]azepine-4-carboxylate and 4-(pyrrolidine-1-carbonyl)phenylboronic acid. The reaction product from the cross-coupling reaction is purified by preparative LC. Following purification, an N—BOC deprotection step is carried out using TFA:DCM.

The use of metal-catalyzed cross-coupling reactions allows the preparation of 8-substituted benzazepine derivatives such as (1E,4E)-ethyl-2-amino-8-(4-(pyrrolidine-1-carbonyl)phenyl)-3H-benzo[b]azepine-4-carboxylate and the like. However, the palladium catalyst used in such reactions presents challenging purification obstacles. For example, where the benzazepine product is to be used as a pharmaceutically active agent, residual palladium waste left after the Suzuki reaction must be removed such that the concentration of palladium metal is within levels that are acceptable for pharmaceutical compositions. An ideal method of synthesizing benzazepine derivatives would, for example, provide product compounds in high yield with low levels of metal contamination. Preferably, such methods would avoid or minimize the use of purification by chromatographic methods. The present invention is directed at providing one or more of these desirable features.

SUMMARY OF THE DISCLOSURE

The present disclosure describes methods for preparing substituted benzazepine compounds. In one embodiment, for example, the disclosure describes methods for preparing {2-amino-8-[4-(pyrrolidinylcarbonyl)phenyl]-(3H-benzo[f]azepin-4-yl)}-N,N-dipropylcarboxamide (herein "HG4"). It is preferred that such methods allow for preparation of HG4 having low levels of metal impurities and/or preparation of HG4 on a large-scale without the need for purification by chromatography.

In one embodiment, then, the disclosure describes an improved method for preparing {2-amino-8-[4-(pyrrolidinylcarbonyl)phenyl]-(3H-benzo[f]azepin-4-yl)}-N,N-dipropylcarboxamide. The improvement comprises purifying a solution of (tert-butoxy)-N-{4-(N,N-dipropylcarbamoyl)-8-[4-(pyrrolidinylcarbonyl)phenyl](3H-benzo[f]azepin-2-yl) } carboxamide by admixing the solution with a palladium scavenger. The (tert-butoxy)-N-{4-(N,N-dipropylcarbamoyl)-8-[4-(pyrrolidinylcarbonyl)phenyl](3H-benzo azepin-2-yl)}carboxamide is reacted with a protecting-group removal agent to provide {2-amino-8-[4-(pyrrolidinylcarbonyl)phenyl]-(3H-benzo[f]azepin-4-yl)}-N,N-dipropylcarboxamide. The palladium scavenger is selected from: (i) silica beads functionalized with a functional group selected from —$(CH_2)_3$—$NH_2$, —$(CH_2)_3$—SH, —$(CH_2)_3$—NH—C(=S)—NHMe, and —$(CH_2)_3$—NH—$(CH_2)_2$—NH—$(CH_2)_2$—$NH_2$; (ii) polystyrene beads functionalized with a functional group selected from —$CH_2$—NH—C(=S)—$NH_2$ and —$C_6H_4$—$CH_2$—$NH_2$; and (iii) porous carbon particles having a surface area of at least about 1200 $m^2/g$, an average pore diameter of about 1 nm, and a particle diameter of about 0.3 mm to about 0.8 mm.

In another embodiment, the disclosure provides a method for synthesizing purified {2-amino-8-[4-(pyrrolidinylcarbonyl)phenyl]-(3H-benzo[f]azepin-4-yl)}-N,N-dipropylcarboxamide, the method comprising: (a) contacting {2-[(tert-butoxy)carbonylamino]-8-bromo-(3H-benzo[f]azepin-4-yl)}-N,N-dipropylcarboxamide with 4-pyrrolidinylcarbonylphenylboronic acid in the presence of $Pd(OAc)_2$ and ethanol to form a crude product comprising (tert-butoxy)-N-{4-(N,N-dipropylcarbamoyl)-8-[4-(pyrrolidinylcarbonyl)phenyl](3H-benzo[f]azepin-2-yl)}carboxamide, ethanol and impurities; (b) treating the crude product with a palladium scavenger; (c) filtering the treated crude product to provide a purified (tert-butoxy)-N-{4-(N,N-dipropylcarbamoyl)-8-[4-(pyrrolidinylcarbonyl)phenyl](3H-benzo[f]azepin-2-yl)}carboxamide; and (d) contacting the (tert-butoxy)-N-{4-(N,N-dipropylcarbamoyl)-8-[4-(pyrrolidinylcarbonyl)phenyl](3H-benzo[f]azepin-2-yl)}carboxamide with a protecting-group removal agent to provide purified {2-amino-8-[4-(pyrrolidinylcarbonyl)phenyl]-(3H-benzo[f]azepin-4-yl)}-N,N-dipropylcarboxamide, wherein the palladium scavenger is selected from: (i) silica beads functionalized with a functional group selected from —(CH$_2$)$_3$—NH$_2$, —(CH$_2$)$_3$—SH, —(CH$_2$)$_3$—NH—C(═S)—NHMe, and —(CH$_2$)$_3$—NH—(CH$_2$)$_2$—NH—(CH$_2$)$_2$—NH$_2$; (ii) polystyrene beads functionalized with a functional group selected from —CH$_2$—NH—C(═S)—NH$_2$ and —C$_6$H$_4$—CH$_2$—NH$_2$; and (iii) porous carbon particles having a surface area of at least about 1200 m$^2$/g, an average pore diameter of about 1 nm, and a particle diameter of about 0.3 mm to about 0.8 mm. In some such embodiments, the purified {2-amino-8-[4-(pyrrolidinylcarbonyl)phenyl]-(3H-benzo[f]azepin-4-yl)}-N,N-dipropylcarboxamide has a purity of at least 98% as measured by HPLC. In other such embodiments, in the purified {2-amino-8-[4-(pyrrolidinylcarbonyl)phenyl]-(3H-benzo[f]azepin-4-yl)}-N,N-dipropylcarboxamide, no more than one impurity is present in an amount that is greater than about 0.5%.

In another embodiment, the disclosure describes a method for synthesizing purified {2-amino-8-[4-(pyrrolidinylcarbonyl)phenyl]-(3H-benzo[f]azepin-4-yl)}-N,N-dipropylcarboxamide. The method comprises contacting {2-[(tert-butoxy)carbonylamino]-8-bromo-(3H-benzo[f]azepin-4-yl)}-N,N-dipropylcarboxamide with 4-pyrrolidinylcarbonylphenylboronic acid in the presence of Pd(OAc)$_2$ and ethanol to form a crude product comprising (tert-butoxy)-N-{4-(N,N-dipropylcarbamoyl)-8-[4-(pyrrolidinylcarbonyl)phenyl](3H-benzo[f]azepin-2-yl)}carboxamide, ethanol and impurities. The crude product is treated with a palladium scavenger. The treated crude product is then filtered to provide a purified (tert-butoxy)-N-{4-(N,N-dipropylcarbamoyl)-8-[4-(pyrrolidinylcarbonyl)phenyl](3H-benzo[f]azepin-2-yl)}carboxamide. The (tert-butoxy)-N-{4-(N,N-dipropylcarbamoyl)-8-[4-(pyrrolidinylcarbonyl)phenyl](3H-benzo[f]azepin-2-yl)}carboxamide is then contacted with a protecting-group removal agent to provide purified {2-amino-8-[4-(pyrrolidinylcarbonyl)phenyl]-(3H-benzo[f]azepin-4-yl)}-N,N-dipropylcarboxamide.

In another embodiment, the disclosure describes a composition comprising {2-amino-8-[4-(pyrrolidinylcarbonyl)phenyl]-(3H-benzo[f]azepin-4-yl)}-N,N-dipropylcarboxamide and one or more palladium-containing contaminants. The {2-amino-8-[4-(pyrrolidinylcarbonyl)phenyl]-(3H-benzo[f]azepin-4-yl)}-N,N-dipropylcarboxamide is prepared using a palladium-catalyzed coupling reaction, and the palladium is present in a concentration of less than 20 ppm by ICP-OES.

In another embodiment, the disclosure provides a composition consisting of at least 98% {2-amino-8-[4-(pyrrolidinylcarbonyl)phenyl]-(3H-benzo[f]azepin-4-yl)}-N,N-dipropylcarboxamide and no more than 20 ppm of palladium or palladium-containing compounds.

In still another embodiment, the disclosure describes a method for preparing {2-amino-8-[4-(pyrrolidinylcarbonyl)phenyl]-(3H-benzo[f]azepin-4-yl)}-N,N-dipropylcarboxamide. The method comprises contacting a halogenated benzazepine with a boronic acid in the presence of a palladium catalyst and optionally in the presence of a ligand and a base under substantially anhydrous conditions to produce an aryl-substituted benzazepine. The aryl-substituted benzazepine from is purified by adding a palladium scavenger. The palladium scavenger is selected from: (i) silica beads functionalized with a functional group selected from —(CH$_2$)$_3$—NH$_2$, —(CH$_2$)$_3$—SH, —(CH$_2$)$_3$—NH—C(═S)—NHMe, and —(CH$_2$)$_3$—NH—(CH$_2$)$_2$—NH—(CH$_2$)$_2$—NH$_2$; polystyrene beads functionalized with a functional group selected from —CH$_2$—NH—C(═S)—NH$_2$ and —C$_6$H$_4$—CH$_2$—NH$_2$; and (iii) porous carbon particles having a surface area of at least about 1200 m$^2$/g, an average pore diameter of about 1 nm, and a particle diameter of about 0.3 mm to about 0.8 mm.

In a further embodiment, the disclosure provides a method for preparing a composition. The method comprises contacting a halo-substituted benzazepine with a boronic acid in the presence of a palladium catalyst to provide a crude composition comprising a substituted benzazepine and one or more palladium contaminants. A palladium scavenger is added to the crude composition for a predetermined time. The palladium scavenger is then removed to yield a purified composition comprising a substituted benzazepine and a palladium contaminant. The palladium contaminant is present in a concentration of less than 50 ppm (or, for example, less than 20 ppm) by ICP-OES.

In a further embodiment, the disclosure provides a method for preparing {2-amino-8-[4-(pyrrolidinylcarbonyl)phenyl]-(3H-benzo[f]azepin-4-yl)}-N,N-dipropylcarboxamide. The method comprises contacting a halogenated benzazepine with a boronic acid in the presence of a palladium catalyst and optionally in the presence of a ligand and a base under substantially anhydrous conditions to produce an aryl-substituted benzoazepin. The aryl-substituted benzazepine product is purified by adding a palladium scavenger as described herein. In one embodiment, the halogenated benzazepine is {2-[(tert-butoxy)carbonylamino]-8-bromo-(3H-benzo[f]azepin-4-yl)}-N,N-dipropylcarboxamide, the boronic acid is 4-pyrrolidinylcarbonylphenylboronic acid, and the palladium catalyst is Pd(OAc)$_2$, the ligand and base are present, the ligand is 4,4'-(phenylphosphinidene)bis(benzenesulfonic acid) dipotassium salt hydrate, and the base is Na$_2$CO$_3$.

BRIEF DESCRIPTION OF THE DRAWINGS

FIG. 1 depicts an example of a method for preparing {2-amino-8-[4-(pyrrolidinylcarbonyl)phenyl]-(3H-benzo[f]azepin-4-yl)}-N,N-dipropylcarboxamide as disclosed herein.

DETAILED DESCRIPTION OF THE INVENTION

Unless otherwise indicated, the disclosure is not limited to specific procedures, starting materials, or the like, as such may vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "a reactant" includes not only a single reactant but also a combination or mixture of two or more different reactant, reference to "a substituent" includes a single substituent as well as two or more substituents, and the like.

As used herein, the phrases "for example," "for instance," "such as," or "including" are meant to introduce examples that further clarify more general subject matter. These examples are provided only as an aid for understanding the disclosure, and are not meant to be limiting in any fashion. Furthermore as used herein, the terms "may," "optional," "optionally," or "may optionally" mean that the subsequently described circumstance may or may not occur, so that the description includes instances where the circumstance occurs and instances where it does not. For example, the phrase "optionally present" means that an object may or may not be present, and, thus, the description includes instances wherein the object is present and instances wherein the object is not present.

In describing and claiming the present invention, the following terminology will be used in accordance with the definitions set out below.

As used herein, the phrase "having the formula" or "having the structure" is not intended to be limiting and is used in the same way that the term "comprising" is commonly used. The term "independently selected from" is used herein to indicate that the recited elements, e.g., R groups or the like, can be identical or different.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although not necessarily, alkyl groups herein may contain 1 to about 18 carbon atoms, and such groups may contain 1 to about 12 carbon atoms. The term "lower alkyl" intends an alkyl group of 1 to 6 carbon atoms, for example, 1, 2, 3, 4, 5, or 6 carbon atoms. "Substituted alkyl" refers to alkyl substituted with one or more substituent groups, and the terms "heteroatom-containing alkyl" and "heteroalkyl" refer to an alkyl substituent in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein may contain 2 to about 18 carbon atoms, and for example may contain 2 to 12 carbon atoms. The term "lower alkenyl" intends an alkenyl group of 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein may contain 2 to about 18 carbon atoms, and such groups may further contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "$C_1$-$C_6$ alkoxy" or "lower alkoxy" herein may, for example, may contain 1 to 3 carbon atoms, and as a further example, such substituents may contain 1 or 2 carbon atoms (i.e., methoxy and ethoxy).

The term "aryl" as used herein, and unless otherwise specified, refers to an aromatic substituent generally, although not necessarily, containing 5 to 30 carbon atoms and containing a single aromatic ring or multiple aromatic rings that are fused together, directly linked, or indirectly linked (such that the different aromatic rings are bound to a common group such as a methylene or ethylene moiety). Aryl groups may, for example, contain 5 to 20 carbon atoms, and as a further example, aryl groups may contain 5 to 12 carbon atoms. For example, aryl groups may contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 30 carbon atoms. Aralkyl and alkaryl groups may, for example, contain 6 to 20 carbon atoms, and as a further example, such groups may contain 6 to 12 carbon atoms.

The term "amino" is used herein to refer to the group —$NZ^1Z^2$ wherein $Z^1$ and $Z^2$ are hydrogen or nonhydrogen substituents, with nonhydrogen substituents including, for example, alkyl, aryl, alkenyl, aralkyl, and substituted and/or heteroatom-containing variants thereof.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, furyl, pyrimidinyl, imidazolyl, 1,2,4-triazolyl, tetrazolyl, etc., and examples of heteroatom-containing alicyclic groups are pyrrolidino, morpholino, piperazino, piperidino, tetrahydrofuranyl, etc.

"Hydrocarbyl" refers to univalent hydrocarbyl radicals containing 1 to about 30 carbon atoms, including 1 to about 24 carbon atoms, further including 1 to about 18 carbon atoms, and further including about 1 to 12 carbon atoms, including linear, branched, cyclic, saturated and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation, functional groups and the hydrocarbyl moieties $C_1$-$C_{24}$ alkyl (including $C_1$-$C_{18}$ alkyl, further including $C_1$-$C_{12}$ alkyl, and further including $C_1$-$C_6$ alkyl), $C_2$-$C_{24}$ alkenyl (including $C_2$-$C_{18}$ alkenyl, further including $C_2$-$C_{12}$ alkenyl, and further including $C_2$-$C_6$ alkenyl), $C_2$-$C_{24}$ alkynyl (including $C_2$-$C_{18}$ alkynyl, further including $C_2$-$C_{12}$ alkynyl, and further including $C_2$-$C_6$ alkynyl), $C_5$-$C_{30}$ aryl (including $C_5$-$C_{20}$ aryl, and further including $C_5$-$C_{12}$ aryl), and $C_6$-$C_{30}$ aralkyl (including $C_6$-$C_{20}$ aralkyl, and further including $C_6$-$C_{12}$ aralkyl).

By "functional group," as alluded to in some of the aforementioned definitions, is meant a non-hydrogen group comprising one or more non-hydrocarbon functionality. Examples of functional groups include, without limitation: halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-substituted $C_1$-$C_{24}$ alkylcarbamoyl (—(CO)—NH($C_1$-$C_{24}$ alkyl)), di-substituted alkylcarbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—C≡N), isocyano (—N$^+$≡C$^-$), cyanato (—O—C≡N), isocyanato (—O—N$^+$≡C$^-$), isothiocyanato (—S—C≡N), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{20}$ alkaryl, $C_6$-$C_{20}$ aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfanyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$), mono- and di-($C_1$-$C_{24}$ alkyl)-substituted phosphino, mono- and di-($C_5$-$C_{20}$ aryl)-substituted phosphino; and the hydrocarbyl moieties $C_1$-$C_{24}$ alkyl (including $C_1$-$C_{18}$ alkyl, further including $C_1$-$C_{12}$ alkyl, and further including $C_1$-$C_6$ alkyl), $C_2$-$C_{24}$ alkenyl (including $C_2$-$C_{18}$ alkenyl, further including $C_2$-$C_{12}$ alkenyl, and further including $C_2$-$C_6$ alkenyl), $C_2$-$C_{24}$ alkynyl (including $C_2$-$C_{18}$ alkynyl, further including $C_2$-$C_{12}$ alkynyl, and further including $C_2$-$C_6$ alkynyl), $C_5$-$C_{30}$ aryl (including $C_5$-$C_{20}$ aryl, and further including $C_5$-$C_{12}$ aryl), and $C_6$-$C_{30}$ aralkyl (including $C_6$-$C_{20}$ aralkyl, and further including $C_6$-$C_{12}$ aralkyl). In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

It will be appreciated that some of the abovementioned definitions may overlap, such that some chemical moieties may fall within more than one definition.

When the term "substituted" appears prior to a list of possible substituted groups, it is intended that the term apply to every member of that group. For example, the phrase "substituted alkyl and aryl" is to be interpreted as "substituted alkyl and substituted aryl."

By two moieties being "connected" is intended to include instances wherein the two moieties are directly bonded to each other, as well as instances wherein a linker moiety is present between the two moieties. Linker moieties may include groups such as heteroatoms, $C_1$-$C_{24}$ alkylene (including $C_1$-$C_{18}$ alkylene, further including $C_1$-$C_{12}$ alkylene, and further including $C_1$-$C_6$ alkylene), $C_2$-$C_{24}$ alkenylene (including $C_2$-$C_{18}$ alkenylene, further including $C_2$-$C_{12}$ alkenylene, and further including $C_2$-$C_6$ alkenylene), $C_2$-$C_{24}$ alkynylene (including $C_2$-$C_{18}$ alkynylene, further including $C_2$-$C_{12}$ alkynylene, and further including $C_2$-$C_6$ alkynylene), $C_5$-$C_{30}$ arylene (including $C_5$-$C_{20}$ arylene, and further including $C_5$-$C_{12}$ arylene), and $C_6$-$C_{30}$ aralkylene (including $C_6$-$C_{20}$ aralkylene, and further including $C_6$-$C_{12}$ aralkylene).

The disclosure provides methods of synthesis for substituted benzazepines, particularly aryl substituted 2-aminobenzazepines. In certain aspects, then, the invention provides methods for the preparation of compounds having the structure of formula (I)

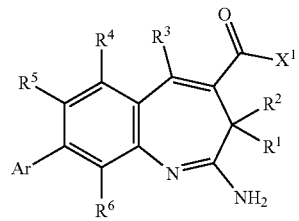

wherein, in formula (I):
$R^1$, $R^2$, $R^3$, $R^4$, $R^5$, and $R^6$ are independently selected from H, $C_1$-$C_{24}$ hydrocarbyl, and functional groups;
$X^1$ is selected from —OR$^7$ and —N(R$^8$)(R$^9$), wherein R$^7$, R$^8$, and R$^9$ are selected from H, and $C_1$-$C_{24}$ hydrocarbyl; and
Ar is an aryl moiety.

In preferred embodiments, $R^1$, $R^2$, $R^3$, $R^4$, $R^5$, and $R^6$ are independently selected from H, $C_1$-$C_{24}$ alkyl (including $C_1$-$C_{18}$ alkyl, further including $C_1$-$C_{12}$ alkyl, and further including $C_1$-$C_6$ alkyl), $C_2$-$C_{24}$ alkenyl (including $C_2$-$C_{18}$ alkenyl, further including $C_2$-$C_{12}$ alkenyl, and further including $C_2$-$C_6$ alkenyl), $C_2$-$C_{24}$ alkynyl (including $C_2$-$C_{18}$ alkynyl, further including $C_2$-$C_{12}$ alkynyl, and further including $C_2$-$C_6$ alkynyl), $C_5$-$C_{30}$ aryl (including $C_5$-$C_{20}$ aryl, and further including $C_5$-$C_{12}$ aryl), and $C_6$-$C_{30}$ aralkyl (including $C_6$-$C_{20}$ aralkyl, and further including $C_6$-$C_{12}$ aralkyl), any of which may be heteroatom-containing with 1, 2, 3 or more heteroatoms and/or substituted with 1, 2, 3 or more substituents. In one preferred embodiment, $R^1$, $R^2$, $R^3$, $R^4$, $R^5$, and $R^6$ are each H.

In preferred embodiments, X is —N(R$^8$)(R$^9$), wherein R$^8$ and R$^9$ are lower alkyl groups. For example, in one embodiment, R$^8$ and R$^9$ are both n-propyl groups. In another embodiment, R$^8$ and R$^9$ are both ethyl groups In preferred embodiments, Ar is selected from substituted or unsubstituted C$_5$-C$_{30}$ arylene (including C$_5$-C$_{20}$ arylene, and further including C$_5$-C$_{12}$ arylene) and substituted or unsubstituted C$_5$-C$_{30}$ heteroarylene (including C$_5$-C$_{20}$ heteroarylene, and further including C$_5$-C$_{12}$ heteroarylene). When Ar is substituted, from 1-5 substituents may be present, and any two or more substituents may be taken together to form one or more annulated rings. The substituents may be selected from any of the groups described previously herein, such as functional groups and hydrocarbyl moieties. In a preferred embodiment, Ar is a substituted phenyl group. For example, Ar has the formula

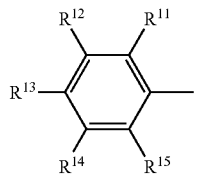

wherein R$^{11}$, R$^{12}$, R$^{13}$, R$^{14}$, and R$^{15}$ are independently selected from H, C$_1$-C$_{24}$ hydrocarbyl, and functional groups. In a preferred embodiment, R$^{11}$, R$^{12}$, R$^{14}$, and R$^{15}$ are H and R$^{13}$ is non-hydrogen, such that Ar is a para-substituted phenyl ring. In one such preferred embodiment, R$^{13}$ is pyrrolidinylcarbonyl.

Compounds having the structure of formula (I) are preferably prepared by a metal-catalyzed cross-coupling reaction between an organoboron compound and a compound having the structure of formula (Ia):

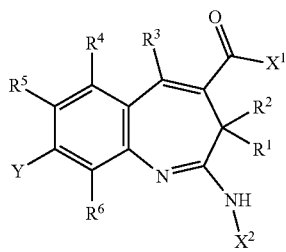

wherein, in formula (Ia):
R$^1$, R$^2$, R$^3$, R$^4$, R$^5$, R$^6$, and X$^1$ are as defined above;
X$^2$ is an amine protecting group; and
Y is an electron withdrawing moiety.

A variety of amine protecting groups are known and described in the chemical literature. For example, such groups are described in Greene, T. W., and Wuts, P., "Protective Group in Organic Synthesis," 3rd Ed., Wiley, New York, 1999. In a preferred embodiment, X$^2$ is a BOC (i.e., t-butyl carbamate) group.

In preferred embodiments, Y is selected from a halo group and a trifluoromethane-sulfonate (triflate) group. In a preferred embodiment, Y is Br or I, with Br being particularly preferred.

In preferred embodiments, the organoboron compound has the structure Ar—B(OR$^{10}$)$_2$, wherein Ar is as defined above, and wherein each R$^{10}$ is selected from H and lower alkyl, and further wherein the two R$^{10}$ groups may be taken together to form a ring. When the two R$^{10}$ groups are taken together to form a ring, the ring may be either alicyclic or aromatic, and may be substituted or unsubstituted. In a preferred embodiment, both R$^{10}$ groups are H.

The metal-catalyzed cross-coupling reaction preferably involves a Pd(0) or Pd(II) catalyst or a precursor thereof. Preferred palladium catalysts are Pd(AcO)$_2$, Pd(PPh$_3$)$_4$, and PdCl$_2$(PPh$_3$)$_2$, with Pd(AcO)$_2$ being particularly preferred.

The cross-coupling reaction may further involve addition of a ligand to the reaction mixture, particularly when a Pd(0) or Pd(II) precursor catalyst is used. Triaryl phosphine ligands are particularly suitable for the cross-coupling reactions, and in a preferred embodiment, the ligand is 4,4'-(phenylphosphinidene)bis(benzenesulfonic acid) dipotassium salt hydrate.

The cross-coupling reaction may further involve addition of a base to the reaction mixture. For example, a preferred base is selected from Na$_2$CO$_3$ and K$_2$CO$_3$. Other bases known in the art may be used such as carbonates, bicarbonates, sulfates, sulfites, and hydroxides of sodium, lithium, magnesium, calcium, or potassium.

The cross-coupling reaction is preferably carried out in a polar solvent such as ethanol. In one preferred embodiment, the reaction is carried out under largely anhydrous conditions. For example, when ethanol is the reaction solvent, "largely anhydrous" conditions may be obtained by using 200 proof ethanol and by not adding bulk water to the reaction. In a preferred embodiment, the ethanol contains less than about 0.5% water, more preferably less than about 0.2% water.

Alternative embodiments of the cross-coupling reaction are also described by reference to the following publications: Miyaura et al. (1995), "Palladium-Catalyzed Cross-Coupling Reactions of Organoboron Compounds," *Chem. Rev.*, 95:2457-2483; and Suzuki (1999), "Recent Advances in the Cross-Coupling Reactions of Organoboron Derivatives with Organic Electrophiles, 1995-1998," *J. Organomet. Chem.*, 576:147-168.

It will be appreciated that, although a wide variety of reaction conditions are suitable to provide the cross-coupling reaction product, certain reaction conditions are most preferred because they yield the greatest amount of product and/or provide a product having the highest purity. In particular, Pd(OAc)$_2$ and 4,4'-(phenylphosphinidene)bis(benzenesulfonic acid) dipotassium salt hydrate are a preferred catalyst and ligand, respectively. The most preferred ratio of catalyst to ligand is within the range of about 1:2 to about 1:1.

It will be appreciated that a deprotection reaction is required in order to complete the transformation from a compound of formula (Ia) to a compound of formula (I). In particular, the amine protecting group X$^2$ must be removed in order to obtain the free amine present in formula (I). Thus, in one embodiment, the cross-coupling reaction described above is carried out with an amine-protected benzazepine derivative having the structure of formula (Ia). Subsequently, the corresponding 2-aminobenzazepine derivative is obtained by deprotecting the product from the cross-coupling reaction.

The cross-coupling reaction performed according to the disclosure creates a crude product that comprises the desired product, the reaction solvent, residual palladium, and other impurities. It will be appreciated that the other impurities may comprise, for example, unreacted starting materials, salts, solvents, and the like. It will further be appreciated that the residual palladium may comprise unreacted Pd(0) or Pd(II) catalyst as well as palladium waste products (e.g., oxidized palladium, palladium salts, etc.).

In some embodiments, the cross-coupling reaction creates a crude product comprising the desired product as well as a lactam impurity. The lactam impurity is believed to have the structure

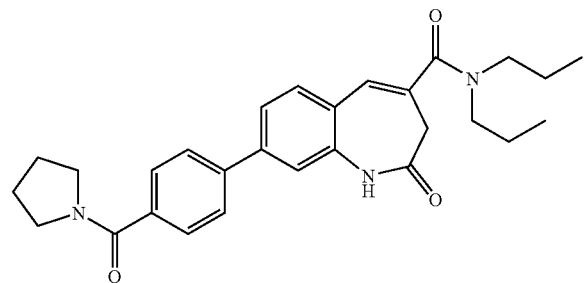

Formation of the lactam impurity can be minimized if the reaction and work-up conditions are kept largely anhydrous, as described above. Alternatively or in addition, the lactam impurity can be removed from the product. A convenient method for removing the lactam impurity involves precipitating the lactam using a trituration in ethyl acetate at room temperature, followed by filtration to remove the lactam.

Removal of the residual palladium may be accomplished using a palladium scavenger. The palladium scavenger is used at any appropriate stage in the work-up of the reaction. Generally, this requires that the crude product is dissolved in a solvent. For example, the palladium scavenger may be added after the crude product has been clarified by an appropriate method such as filtration through diatomaceous earth (e.g., CELITE®), or after performing a solvent exchange to transfer the desired product from the reaction solvent to another solvent. For example, when the cross-coupling reaction is performed in anhydrous ethanol, the palladium scavenger may be added directly to the clarified crude product. Alternatively, and as a further example, the crude product is clarified and then subjected to a solvent exchange such that the ethanol reaction solvent is replaced by ethyl acetate. The palladium scavenger is then added to the resulting ethyl acetate solution.

Residual palladium is thus removed by adding the palladium scavenger to a solution containing the desired product and a solvent, and agitating (e.g., stirring) the resulting slurry. The palladium scavenger is preferably added in a single batch addition. Agitation is generally for a period of time sufficient to allow the concentration of palladium to equilibrate, preferably about 4 hours. The resulting slurry is clarified, for example, by filtration through diatomaceous earth (e.g., CELITE®) or another filtration agent.

The palladium scavenger should be effective to lower the concentration of residual palladium to about 50 ppm or less, or to about 30 ppm or less, or to about 25 ppm or less, or to about 20 ppm or less. The amount of palladium scavenger used in the purification will vary, for example, according to the degree of purification desired, and the identity of the scavenger.

In one embodiment, appropriate palladium scavengers are selected from functionalized silica beads and functionalized polystyrene beads.

In one embodiment, a palladium scavenger suitable to be directly added to the clarified crude product (i.e., a clarified ethanolic solution comprising the desired product and residual palladium) is a composition consisting of functionalized spherical silica beads. In preferred embodiments, the silica beads have a surface area greater than about 500 $m^2/g$, such as, for example, about 715 $m^2/g$, and an average particle size of less than 100 μm, such as, for example, about 50-55 μm. A material meeting these characteristics is sold under the trademark QUADRASIL™. In one preferred embodiment, the silica beads are mercaptopropyl-functionalized (e.g., QUADRASIL™ MP), and in a most preferred embodiment, the silica beads are aminopropyl-funcationalized (e.g., QUADRASIL™ AP). Another palladium scavenger suitable for purifying the clarified crude product is a composition consisting of porous, spherical, non-functional carbon particles with a high surface area (i.e., greater than 1000 $m^2/g$, including, for example, about 1200 $m^2/g$, or at least about 1200 $m^2/g$, or about 1500-1700 $m^2/g$), an average pore diameter of less than about 5 nm (including, for example, about 1 nm), and regular spheroid particles having a diameter of about 0.3 mm to about 0.8 mm. A suitable material meeting with these characteristics is sold under the trademark QUADRAPURE™ C. In some preferred embodiments, such scavengers will be used in an amount up to 1000% wt/wt (with respect to the reactant in the coupling reaction such as, for example, HG1), or within the range of about 50-650% wt/wt, or between about 100 and 650% wt/wt, or between about 200 and 650% wt/wt. Alternatively, the amount of scavenger used in purification can be measured as a concentration. In some embodiments, the scavenger may be used in a concentration of between about 10 mg/mL and about 100 mg/mL, or between about 25 mg/mL and about 75 mg/mL, or about 50 mg/mL.

A palladium scavenger suitable to be added to an ethyl acetate solution comprising the desired product and residual palladium (i.e., the crude product after completing a solvent exchange from ethanol) consists of functionalized spherical silica beads having the physical characteristics described previously. In preferred embodiments, the silica beads are functionalized with a functional group selected from aminopropyl (i.e., —$(CH_2)_3$—$NH_2$), mercaptopropyl (i.e., —$(CH_2)_3$—SH), methylthiourea (i.e., —$(CH_2)_3$—NH—C(=S)—NHMe), and triamine (i.e., —$(CH_2)_3$—NH—$(CH_2)_2$—NH—$(CH_2)_2$—$NH_2$). Examples of such materials are sold under the trademarks QUADRASIL™ AP, QUADRASIL™ MP, QUADRASIL™ MTU, and QUADRASIL™ TA, respectively. Another suitable palladium scavenger under these conditions is a composition consisting of functionalized macroporous polystyrene beads having an average diameter less than about 700 μm, such as, for example, in the range of about 450-600 μm. A material meeting these characteristics is sold under the trademark QUADRAPURE™. In a preferred embodiment, the polystyrene particles are benzylamine-functionalized (e.g., QUADRAPURE™ BZA), and in a most preferred embodiment, the polystyrene beads are thiourea-functionalized (e.g., QUADRAPURE™ TU). Again, in preferred embodiments, such scavengers will be used in the amounts (i.e., wt/wt ranges or concentrations) as mentioned previously.

Alternatively to the above-described methods, purification with a palladium scavenger may be carried out after the product of the cross-coupling reaction has been carried forward through further synthetic steps, such as removal of an amine protecting group.

The method for preparing a 2-aminobenzazepine may comprise further purification steps. For example, after removal of the amine-protecting group (i.e., $X^2$), the compound of formula (I) may be recrystallized one or more times and/or triturated one or more times. Other methods of purification include, for example, solvent switch techniques and chromatography. In preferred embodiments, however, no chromatography steps are involved in the removal of palladium impurities from the 2-aminobenzazepines as described herein.

One preferred embodiment of the invention is depicted in FIG. 1. The FIGURE shows an improved method for preparing {2-amino-8-[4-(pyrrolidinylcarbonyl)phenyl]-(3H-benzo[f]azepin-4-yl)}-N,N-dipropylcarboxamide (i.e., HG4). Reactions (i)-(x) are described in the following disclosure.

With reference to reaction (i) in FIG. 1, (E)-1-(4-bromo-2-nitrostyryl)pyrrolidine (i.e., HF3) is prepared by combining 4-bromo-2-nitrotoluene with N,N-dimethylformamide dimethylacetal, pyrrolidine, and dimethylformamide.

Subsequently, and with reference to reaction (ii) in FIG. 1, 4-bromo-2-nitrobenzaldehyde (i.e., HF4) is prepared by contacting HF3 with $NaIO_4$, wherein the contacting is carried out in solution. In the specific embodiment shown in FIG. 1, the reaction is carried out in $THF:H_2O$ (1:1) solution.

In the enamine formation (i.e., reaction (i)) and the oxidation reaction (i.e., reaction (ii)), the operating temperature is maintained below 110° C. at all times.

Separately, and with reference to reaction (iii) in FIG. 1, ethyl-3-cyano-2-(triphenylphosphanylidine)propanoate (i.e., HF6) is prepared by contacting (carbethoxymethylene)triphenylphosphorane (i.e., HF5) with $BrCH_2CN$, wherein the contacting is carried out in solution. In the specific embodiment shown in FIG. 1, the reaction is carried out in ethyl acetate.

Subsequently, and with reference to reaction (iv) in FIG. 1, (E)-ethyl-3-(4-bromo-2-nitrophenyl)-2-(cyanomethyl)acrylate (i.e., HF7) is prepared by contacting HF4 with HF6, wherein the contacting is carried out in solution and a temperature within the range of about 20° C. to about 25° C. In the specific embodiment shown in FIG. 1, the reaction is carried out in toluene. In preferred methods as described herein, purification of HF7 by column chromatography is not necessary.

Subsequently, and with reference to reaction (v) in FIG. 1, (1E,4E)-ethyl-2-amino-8-bromo-3H-benzo[b]azepin-4-carboxylate (i.e., HF8) is prepared by contacting HF7 with Fe, under conditions effective to cause reduction and intramolecular cyclization. In the specific embodiment shown in FIG. 1, the reaction is carried out in acetic acid at a temperature of 85° C. In preferred embodiments, purification of HF8 by column chromatography is not necessary.

In preferred embodiments of the Fe-reduction reaction, minimal amounts of Fe are used. Thus, improved results can be obtained using about three equivalents of Fe, as compared with reactions using higher amounts. Without wishing to be bound by theory, it is believed that excess Fe lowers the product yield by binding to the product. Some of the product is lost when the Fe is removed during purification.

Subsequently, and with reference to reaction (vi) in FIG. 1, ethyl 2-[(tert-butoxy)carbonylamino]-8-bromo-3H-benzo[b]azepin-4-carboxylate (i.e., HF9) is prepared by contacting HF8 with di-tert-butyl dicarbonate, wherein the contacting is carried out in solution. In the specific embodiment shown in FIG. 1, the reaction is carried out in dichloromethane.

Subsequently, and with reference to reaction (vii) in FIG. 1, 2-[(tert-butoxy)carbonylamino]-8-bromo-3H-benzo[f]azepin-4-carboxylic acid (i.e., HG0) is prepared by contacting HF9 with sodium hydroxide, wherein the contacting is carried out in solution. In the specific embodiment shown in FIG. 1, the reaction is carried out in THF and using 1 M NaOH.

The use of NaOH provides a preferred method for formation of the acid as compared with the use of other bases, such as LiOH. Furthermore, in preferred embodiments of the base hydrolysis reaction, forming a slurry of the HG0 product in ethyl acetate and subsequent filtration represents an improved method for increasing the purity of the HG0 product.

Subsequently, and with reference to reaction (viii) in FIG. 1, {2-[(tert-butoxy)carbonylamino]-8-bromo-(3H-benzo[f]azepin-4-yl)}-N,N-dipropylcarboxamide (i.e., HG1) is prepared by contacting HG0 with diisopropylamine in the presence of 1-ethyl-3-[3-dimethylaminopropyl]carbodiimide hydrochloride (i.e., EDC) and HOBt (hydroxybenzotriazole), wherein the contacting is carried out in solution. In the specific embodiment shown in FIG. 1, the reaction is carried out in dichloromethane.

Formation of the amide prior to carrying out the metal catalyzed cross-coupling reaction (for a description of the cross-coupling reaction, see description for reaction (ix), below) represents a preferred method over the alternative scheme, i.e., formation of the amide after carrying out the cross-coupling reaction. The amide undergoes the cross-coupling reaction with greater efficiency than the corresponding ester compound (e.g., HF9).

Subsequently, and with reference to reaction (ix) in FIG. 1, (tert-butoxy)-N-{4-(N,N-dipropylcarbamoyl)-8-[4-(pyrrolidinylcarbonyl)phenyl](3H-benzo[f]azepin-2-yl)}carboxamide (i.e., HG3) is prepared via a cross-coupling reaction. Thus, HG1 is contacted with 4-pyrrolidinylcarbonylphenylboronic acid (HG2) in the presence of a palladium catalyst and optionally in the presence of a ligand and a base. The contacting is carried out in a solvent and under substantially anhydrous conditions, such that a crude solution comprising HG3 and residual palladium contaminants is prepared. In the specific embodiment shown in FIG. 1, the solvent is 200 proof ethanol, the catalyst is $Pd(OAc)_2$, the ligand is present and is 4,4'-(phenylphosphinidene)bis(benzenesulfonic acid) dipotassium salt hydrate, and the base is present and is $Na_2CO_3$. The reaction is carried out under reflux conditions.

As described herein, the reaction is preferentially carried out under anhydrous conditions. Under preferred conditions, anhydrous and denatured ethanol is used as the solvent. This represents a preferred method over cross-coupling reactions carried out in the presence of water, as the product is more pure and is prepared in higher yield. Furthermore, in preferred methods, the cross-coupling reaction product is partially purified by performing a solvent switch (as described in more detail below), thereby precipitating the boronic acid.

The crude solution of HG3 comprises HG3 and residual palladium, and is purified using a palladium scavenger, as described herein. In a preferred embodiment, as described herein, the purification is carried out on an ethanolic solution of HG3 using a composition consisting of aminopropyl-functionalized spherical silica beads (e.g., QUADRASIL™ AP) or an activated carbon composition such as QUADRAPURE™ C. In another preferred embodiment, and as described herein, a solvent exchange procedure is carried out on the crude solution of HG3, thus providing an ethyl acetate solution of HG3. The purification is then carried out on the ethyl acetate solution of HG3 using mesoporous spherical silica beads functionalized with a functional group selected from aminopropyl (i.e., —$(CH_2)_3$—$NH_2$), mercaptopropyl (i.e., —$(CH_2)_3$—SH), methylthiourea (i.e., —$(CH_2)_3$—NH—C(=S)—NHMe), and triamine (i.e., —$(CH_2)_3$—NH—$(CH_2)_2$—NH—$(CH_2)_2$—$NH_2$), or thiourea-functionalized polystyrene beads. In some preferred embodiments, depalladation is carried out on HG3 using QUADRASIL™ MP (i.e., spherical silica beads functionalized with mercaptopropyl groups). In some preferred embodiments, depalladation is carried out on HG3 using QUADRASIL™ TA (i.e., spherical silica beads functionalized with triamine groups). In some preferred embodiments, depalladation is carried out on HG3 using QUADRASIL™ MTU (i.e., spherical silica beads functionalized with methylthiourea groups). In some preferred embodiments, depalladation is carried out on HG3 using QUADRASIL™ AP (i.e., spherical silica beads functionalized with amino propyl groups). In some preferred embodiments, depalladation is carried out on HG3 using QUADRAPURE™ TU (i.e., polystyrene beads functionalized with thiourea groups). In some preferred embodiments, depalladation is carried out on HG3 using QUADRAPURE™ C (i.e., activated carbon having a surface area of about 1200 m$^2$/g). In some preferred embodiments, depalladation is carried out on HG3 using QUADRAPURE™ BZA (i.e., polystyrene beads functionalized with benzyl amine groups).

Subsequently, and with reference to reaction (x) in FIG. 1, HG3 is reacted with a protecting-group removal agent to provide HG4. In the specific embodiment shown in FIG. 1, the protecting-group removal agent is trifluoroacetic acid, and the reaction is carried out in dichloromethane solvent. When the reaction has reached completion, the batch volume is reduced to about 1 volume DMC with respect to the original amount of HG1 used in the reaction. The HG4 product is precipitated from solution by addition of 4 volumes of EtOAc at room temperature. The product is isolated by filtration, and washed with EtOAc and heptanes. Optionally, the product can be further purified by trituration with DCM/EtOAc (1:4).

Optionally, the isolated HG4 product can be even farther purified by one or more recrystallizations. In a preferred embodiment, a DCM/cyclohexane solvent system is used to recrystallize the product. The product is then repeatedly triturated in EtOAc and washed with EtOAc and cyclohexane until the desired purity is reached.

In preferred embodiments, the transformation from HG1 to HG4 is carried out such that HG4 is obtained in at least 15%, or at least 20%, or at least 25% yield from HG1. In addition, HG4 prepared according to preferred embodiments has a purity of at least 98%, or at least 98.5% as measured by HPLC. Furthermore, HG4 prepared according to preferred embodiments contains no more than one impurity that is present in an amount that is greater than about 0.5%. For example, in preferred embodiments, one impurity is present in an amount that is greater than 0.2%, and all other impurities are present in an amount less than 0.2%. In some preferred embodiments, the final HG4 prepared according to the invention comprises the lactam impurity in an amount less than or equal to 0.62% (as measured by HPLC as described herein in the examples), and no other impurity in an amount greater than 0.20%. In some preferred embodiments, the final HG4 prepared according to the invention comprises the lactam impurity in an amount less than or equal to 0.60% (as measured by HPLC as described herein in the examples), and no other impurity in an amount greater than 0.20%.

In preferred embodiments of the methods disclosed herein, the methods provide a composition comprising {2-amino-8-[4-(pyrrolidinylcarbonyl)phenyl]-(3H-benzo[f]azepin-4-yl)}-N,N-dipropylcarboxamide and a palladium residue, wherein the palladium is present in a concentration of less than about 50 ppm, or less than about 30 ppm, or less than about 20 ppm, or less than about 15 ppm, or less than about 10 ppm by Inductively Coupled Plasma-Optical Emission Spectroscopy (ICP-OES).

It will be appreciated that the methods disclosed herein are suitable for both large-scale and small-scale preparations of the desired compounds. In preferred embodiments of the methods described herein, the benzazepine may be prepared on a large scale, for example on an industrial production scale rather than on an experimental/laboratory scale. For example, a batch-type process according to the methods of the disclosure allows the preparation of batches of at least 1 g, or at least 5 g, or at least 10 g, or at least 100 g, or at least 1 kg, or at least 100 kg of benzazepine product. Furthermore, the methods allow the preparation of a benzazepine product having a purity of at least 98%, or at least 98.5% as measured by HPLC. Furthermore, the methods allow the preparation of a benzazepine product containing no more than one impurity that is present in an amount that is greater than about 0.5%. For example, in preferred embodiments, one impurity is present in an amount that is greater than 0.2%, and all other impurities are present in an amount less than 0.2%. In preferred embodiments according to the disclosure, these products are obtained in a reaction sequence that does not involve purification by any form of chromatography (e.g., gas chromatography, HPLC, preparative LC, size exclusion chromatography, and the like).

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

It is to be understood that while the invention has been described in conjunction with the preferred specific embodiments thereof, that the foregoing description as well as the examples that follow, are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains.

EXAMPLES

Example 1

Preparation of enamine HF3 from 4-bromo-2-nitrotoluene

Two 250 g batches were performed using DMF-DMA, DMF, pyrrolidine, 96-100° C., 4 h. The general procedure used was as follows. A three-necked round-bottomed flask is equipped with a mechanical stirrer, condenser, thermometer, and nitrogen inlet in a heating mantle. Dimethylformamide and 4-Bromo-2-nitrotoluene were added to the flask and the contents stirred until a solution forms. Charged Pyrrolidine followed by DMF-DMA to the flask. Heated the reaction to reflux (96° C. to 100° C.) and maintained at reflux for approximately 4 hours. Monitored the reaction by TLC. The completed reaction mixture was concentrated on a rotary evaporator (50° C.) to approximately 2 volumes with respect to the product. Product isolation was conducted by two different strategies. First, the concentrated batch was dispensed into methanol (2 volumes) under high agitation, or second, the concentrated batch mixture under a high rate of agitation was charged with methanol (2 volumes). In both instances, the resulting batch medium was a thick suspension. Filtered and dried under vacuum at 35° C. This effort afforded two 290 g (84% yield 98.2% or 95.8% w/w by $^1$H NMR assay) samples of HF3 (Table 2).

Complete conversion was observed after approximately 4 hours of heating at 96-100° C. A completed reaction mixture was left standing at ambient temperature for a period of 3 days and exhibited stability as no change in the HPLC purity of HF3 was observed.

Both the starting material and product contain an aryl nitro moiety. Differential scanning calorimetry (DSC) data for HF2 and HF3 was acquired to ensure the synthetic process was not operating too closely to the recorded onset temperatures (Table 1). Both materials were found to be highly energetic. Due to the low observed onset temperature of HF3: 125° C. and high observed energies of HF2: 1843 J/g and HF3: 1549 J/g, the Step 1 operating temperature (100-105° C.) was not allowed to exceed 110° C. at any point during the process.

TABLE 1

DSC data for HF2 and HF3

| Compound | Lot # | Observed onset temp (° C.) | Observed energy (J/g) |
| --- | --- | --- | --- |
| HF2 | Aldrich (10621CE)) | 271 | 1843 |
| HF3 | 176-1 | 125 | 1549 |

TABLE 2

Summary of manufactured enamine HF3.

| HF3 Lot # | Crude isolated mass (g) | $^1$H NMR assay$^A$ (% w/w) | Actual mass (g) | Yield (%) |
| --- | --- | --- | --- | --- |
| 030-1 | 295.39 | 98.2 | 290.07 | 84 |
| 032-1 | 305.96 | 95.8 | 290.03 | 84 |

$^A$$^1$H NMR spectra were run at 400 MHz in CDCl$_3$.

Example 2

Oxidative cleavage of enamine HF3 to afford 4-bromo-2-nitrobenzaldehyde

The experimental procedure involved the following conditions: NaIO$_4$, THF:H$_2$O, 0-5 to 25° C., 18 h. The general procedure is as follows. Equipped a three-necked round-bottomed flask with a mechanical stirrer and thermocouple in a cooling tub. Charged Water and Sodium periodate to the flask and stirred for 10 minutes. Cooled the reaction to ~10° C. using an Ice/Water bath. Added THF to the reaction in a single portion. Continue cooling the reaction to 0° C. to 5° C. Prepared a solution by dissolving (E)-1-(4-Bromo-2-nitrostyryl) pyrrolidine (1160 g, 3.90 mol) in THF (3 L). Added this solution in a thin stream to the reaction at <5° C. Allowed the reaction mixture to warm to room temperature overnight. Monitored the reaction by TLC. The reaction is complete when no starting material is observed. Isolated product by filtering to remove the solids. Washed the solids twice with Ethyl acetate. Combined all of the filtrates in a separatory funnel, allowed the layers to separate and collect the organic layer. Extracted the aqueous layer three times with EtOAc. Washed the combined organics with Water and Brine. Dried the organic solution over Magnesium sulfate and charcoal, filtered and concentrated the filtrate to a thick yellow suspension. Slurried the solids in Ethyl ether and cooled to −10° C. to −20° C. Filtered to collect the solids and washed with cold (−20° C.) Ethyl ether. Dried at ambient temperature as a yellow powder.

The batch was run on 550 g of enamine. This effort afforded 340.9 g of product, which contained 6.5% w/w of water ($^1$H NMR, DMSO-d$_6$). Therefore, a final calculated mass of 318.7 g (74% yield, 99.4% a/a by HPLC) was obtained.

The reaction progress was monitored by TLC (20% EtOAc in heptanes) and HPLC. Complete conversion was observed upon agitation of the batch overnight while allowing the batch temperature to rise from 0-5° C. to 20-25° C. Both the starting material and product contain an aryl nitro moiety. Differential scanning calorimetry (DSC) data for HF3 and HF4 was acquired to ensure the synthetic process was not operating too closely to the recorded onset temperatures (see Table 3). Table 4 provides a summary of manufactured aldehyde HF4.

TABLE 3

DSC data for aldehyde HF4

| Compound | Lot # | Observed onset temp (° C.) | Observed energy (J/g) |
| --- | --- | --- | --- |
| HF3 | 176-1 | 125 | 1549 |
| HF4 | 184-2 | 211 | 2005 |
| HF4 distillation residue | 184-1 | 188.3 | 1730 |

TABLE 4

Summary of manufactured aldehyde HF4.

| HF4 Lot # | Crude isolated mass (g) | $^1$H NMR assay$^A$ (% w/w) | Actual mass (g) | Yield (%) |
| --- | --- | --- | --- | --- |
| 199-2 | 340.9 | 93.5 | 318.7 | 74 |

$^A$$^1$H NMR spectra were run at 400 MHz in DMSO-d$_6$.
Analysis revealed that HF4 contained 6.5% w/w of water.

Example 3

Preparation of Phosphorane HF6

The Wittig precursor HF6 was prepared using the following conditions: BrCH$_2$CN, EtOAc, reflux. To a flask equipped with a mechanical stirrer, condenser, thermocouple, nitrogen inlet, and drying tube in a heating mantle was added ethyl acetate (7.8 vol) and ethyl 2-(triphenylphosphanylidene)acetate (HF5). Charged the bromoacetonitrile and heated the reaction to reflux (77° C.) and maintained at reflux overnight. Monitored reaction progress by HPLC. The reaction is complete when <3% starting material is observed.

To isolate the product, the reaction is cooled to room temperature, filtered to remove the solids and the solids washed twice with ethyl acetate. Evaporated to remove approximately half of the solvent. Washed the organic concentrate with Brine. Dried the organics with Magnesium sulfate; filtered and evaporated under vacuum to a concentrated solution. Discontinued vacuum and diluted the residue with ethyl ether while stirring until solids precipitated (~40 minutes). Transferred the slurry to a 2 gallon pail equipped with mechanical stirring. Diluted the slurry further with heptane and stirred for an additional 30 to 60 minutes. Filtered the solids onto a 13" crock filter and washed twice with 1:1 heptane/ethyl ether. Dried under vacuum at 30° C. to 35° C.

The dilution of ethyl acetate could be reduced from 7.8 to 2.6 volumes. Using the more concentrated conditions, there was no negative impact on product quality. Based on 1159 g of HF5, an isolated HF6 mass of 588 g (91% yield, >98% a/a by HPLC) was obtained.

One equivalent of ethyl 2-(triphenylphosphanylidene)acetate is consumed during the reaction to scavenge the HBr formed in the reaction. Efficiency may be enhanced by incorporation of a trialkylamine base.

Reactions were completed on 3.2 g scale of HF5. The reaction progress was monitored by TLC (60% EtOAc in heptanes) and HPLC.

Large scale reactions used 1159 g of HF5 and about 200 g of $BrCH_2CN$, and 3 L of EtOAc (about 2.6 volumes with respect to HF5). Monitoring of the reaction progress by TLC and HPLC, showed no negative impact on product quality as a result of running the batch more concentrated.

Differential scanning calorimetry (DSC) data and manufacturing data for HF5 and HF6 was acquired as tabulated in Tables 5 and 6.

TABLE 5

Summary of manufactured HF6.

| HF6 Lot # | Isolated mass (g) | Yield (%) | HPLC purity (% a/a) |
|---|---|---|---|
| 135-1 | 588 | 91 | >98 |

TABLE 6

DSC data for HF5 and HF6.

| Compound | Lot # | Observed onset temp (° C.) | Observed energy (J/g) |
|---|---|---|---|
| HF5 | Aldrich | 231 | 109.0 |
| HF6 | 135-1 | 182 | 75.8 |

Example 4

Wittig Reaction of Phosphorane HF6 and Aldehyde HF4 to Afford Acrylate HF7

The Wittig coupling was performed in toluene solvent. Reactions were performed either at elevated temperatures or maintained at 20-25° C. while monitoring for the consumption of the HF4. The low temperature procedure afforded 87% yield of HF7. The purity was not determined for this batch.

The general procedure is as follows. To a three-necked round-bottomed flask in a heating mantle with a mechanical stirrer, nitrogen inlet, drying tube, thermocouple probe and a reflux condenser was charged 4-Bromo-2-nitrobenzaldehyde (1.0 eq), Toluene (16 vol) and Ethyl 3-cyano-2-(triphenylylidene) propanoate (1.1 eq). Heated and stirred the dark brown clear reaction mixture for 2 hours at either elevated temperature or room temperature. Reaction is complete when no starting material is observed. Product was isolated by cooling the reaction mixture to ~26° C. and filtering to remove un-dissolved salts; rinsed the filter twice with toluene. Evaporated the filtrate to dryness as a dark brown semi solid on a rotoevaporator at reduced pressure and water bath temperature ~45° C. Triturated with heptane, and stirred manually briefly. Decanted a majority of the heptane before filtering the remainder of the mixture to collect the solids. Rinsed twice with heptane and air dried for 2 hours. Suspended the crude product in methanol, stirring for 30 minutes at room temperature. Continued to stir until all clumps of solids have been broken up, leaving a thin slurry of fine solids. Let the suspension stand in the freezer overnight. Filtered to collect the off-white solids and rinsed twice with pre-chilled (−20° C.) MeOH. Dried the product under vacuum at 30° C. for 5 hours; continued to dry at room temperature.

For the high temperature method, the starting materials HF4 and HF6 were combined in toluene and heated to 100-105° C. The HF4 feedstock containing 6.5% w/w of water. Excess water was azeotropically removed during the initial batch heating. The reaction mass typically developed a black color upon heating to 100° C. Reaction progress was monitored by TLC (66% EtOAc in heptanes) and HPLC. This afforded yields of about 48-53% of HF7. The isolated yields were largely attributed to low assays of the HF7 product in the crude batch mixture. Improved internal assays (>95% a/a of desired HF7) were achieved when the Wittig chemistry was performed at 20-25° C. The improved HF7 assays resulted in expedient crystallizations of the product in the final isolation solvent (MeOH) and ultimately higher isolated yields (87%). For the low temperature method, in some embodiments the HF4 feedstock should have a low water content (i.e. low KF value). Acquired data is presented in Table 7.

TABLE 7

Summary of manufactured HF7.

| HF7 Lot # | Reaction temp (° C.) | HF4 mass (g) | Isolated mass (g) | Yield (%) | HPLC purity (% a/a) |
|---|---|---|---|---|---|
| 143-1 | 100-105 | 8.93 | 7.0 | 53 | >98 |
| 145-1 | 100-105 | 310 | 220 | 48 | 95.5 |
| 021 | 80-85 | 5.5 | 5.3 | 66 | Not determined |
| 023 | 20-25 | 5.5 | 7.0 | 87 | Not determined |
| 023 | 20-25 | 133.5 | 171.2 | 87 | Not determined |

Example 5

Fe-Reduction and Cyclization of Nitro Compound HF7 to Afford Amidine HF8

The Fe reduction of HF7 and intramolecular cyclization of the intermediate aniline afforded the desired amidine HF8. The Fe-reduction of HF7 was preformed under the following conditions: 3.0 equivalents of Fe powder (about 325 mesh), AcOH, 80-85° C. Starting from 47.5 g of HF7, an isolated HF8 mass of 38.2 g (88% yield, 96.1% a/a by HPLC) was obtained.

The general procedure was as follows: Equipped a three-necked round-bottomed flask in a heating mantle with a mechanical stirrer, nitrogen inlet, drying tube, thermocouple probe and a reflux condenser. Charged the flask with HF7 (1.0 eq) and glacial acetic acid (19 vol) and heated the light yellow clear solution to 80° C. to 85° C. Added Iron powder (325 mesh, 6.2 eq) portion wise over 2 hours keeping the reaction temperature <90° C. and stirred the off-white suspension for another 3 hours at 80° C. to 85° C. Early additions are done at 20 to 30 minutes intervals. After the exotherm diminishes the addition rate can be increased. Monitored the reaction progression by TLC. The reaction is complete when <2% of starting material remains. Isolation of the product was accomplished by cooling the reaction mixture to room temperature and filtering through a celite pad, then rinsing three times with glacial acetic acid. Evaporated the combined filtrate to an oil at reduced pressure on a rotary evaporator. Diluted with cold water and adjusted pH to >8 with saturated sodium bicarbonate solution. Added ethyl acetate to the off-white to light brown suspension while stirring. Filtered the ethyl acetate and water mixture through a crock filter using poly pad. Slurried and re-filtered the brown to off-white solids three times with ethyl acetate. Combined all filtrates, removed the aqueous layer, and washed the combined organic layer with saturated sodium bicarbonate solution, then brine. Combined the aqueous layers and back extracted with ethyl acetate two times. Washed this organic layer with brine. Combined all organic layers, dried over $MgSO_4$, filtered and rinsed twice with ethyl acetate. Concentrated the filtrate to yield light yellow solid slurry on a rotary evaporator. Diluted with diethyl ether, filtered to collect the solids and rinsed them twice with diethyl ether. Air dried the product at ambient temperature overnight. Acquired DSC data are presented in Table 8.

TABLE 8

DSC data for acrylate HF7 and amidine HF8.

| Compound | Lot # | Observed onset temp (° C.) | Observed energy (J/g) |
|---|---|---|---|
| HF7 | 143-1 | 215 | 1115 |
| HF8 | 950-02 | 182 | 34.2 |

Using 3.0 equivalents of Fe facilitated a complete reduction of the nitro moiety within approximately 3 hours of adding the first charge of Fe powder to the batch. Further heating (80-85° C.) of the batch for 3-5 hours completed the cyclization to the desired amidine. This initial effort afforded 38.2 g (88% yield) of HF8, which exhibited a final HPLC purity of 96.1% a/a.

Gelatinous precipitation of Fe derived salts may occur during cooling of the batch and throughout the aqueous workup. This was not observed when Celite (100% w/w with respect to HF7) was added to the cooled batch mixture prior to the initial filtration.

Further batches were performed as tabulated below (Table 9).

TABLE 9

Summary of manufactured HF8.

| HF8 Lot# | HF8 mass (g) | Yield (%) | HPLC purity (% a/a) |
|---|---|---|---|
| 026-1 | 38.2 | 88 | 96.1 |
| 034-4 | 49.0 | 37 | 98.8 |
| 008-1 | 39 | 72 | 98.9 |
| 010-1 | 39 | 73 | 98.7 |
| 012-1 | 43 | 73 | 98.7 |

Example 6

N—BOC-Protection of HF8 to Afford Ester HF9

N—BOC protection of amidine HF8 was performed according to the following conditions: $(Boc)_2O$, TEA, DCM, 0-5 to 25° C. Reaction progress was monitored using HPLC. Starting from 34.0 g of HF8, an isolated HF9 mass of 34.5 g (77% yield, 94.3% a/a by HPLC) was obtained.

The general procedure was as follows. Equipped a three-necked round-bottomed flask in a cooling tub with a mechanical stirrer, nitrogen inlet, drying tube, thermocouple probe and an addition funnel. Charged the flask with HF8 (1.0 eq) and dichloromethane (10 vol) and stirred the off-white suspension for 10 minutes at room temperature. Cooled to ~0° C. and added Triethylamine (1.5 eq) over 10 minutes via the addition funnel at 0° C. to 4° C.; stirred 30 minutes between −5° C. and 0° C. Added a solution of Di-tent-butyl dicarbonate (1.5 eq) in dichloromethane dropwise (to a thin stream) via the addition funnel over 30 minutes at −5° C. to 0° C. Removed the cooling bath and stirred at room temperature over 36 hours. Monitored the reaction progression by TLC and HPLC The reaction is complete when <2% of starting material remains. Isolated the product by quenching the reaction mixture with water. Separated the organic layer and extracted the aqueous layer with dichloromethane. Washed the combined organic layers twice with saturated sodium bicarbonate solution and once with brine. Combined the aqueous layers and two back extracts with dichloromethane. Washed this organic layer with brine. Combined all organic layers, dried over $MgSO_4$, added charcoal, filtered and rinsed twice with dichloromethane. Concentrated the filtrate under vacuum to yield a light yellow solid. Triturated the crude compound with heptane, stirring for a minimum of 1 hour. Collected the solids by filtration and two rinses with heptane. Air dried the product at ambient temperature overnight.

A typical reaction exhibited about 75% conversion to the desired product after 24 hours of agitation. A further 12 to 18 hours was required to consume all of the amidine feedstock. A key impurity observed (RRt 0.96 with respect to HF9) during the synthesis was the lactam by-product. Acquired data is presented in Table 10.

TABLE 10

Summary of manufactured HF9.

| HF9 Lot # | HF9 mass (g) | Yield (%) | HPLC purity (% a/a) |
|---|---|---|---|
| 152-1 | 34.5 | 77 | 94.3 |
| 156-1 | 20.5 | 39 | 94.7 |
| 159-1 | 3.9 | 44 | Not determined |
| 019-1 | 45.5 | 29 | Not determined |

Example 7

Base Hydrolysis of Ester HF9 to Afford Acid HG0

Hydrolysis of ester HF9 with 1M NaOH was performed using the following conditions: THF, −15° C. to 20-25° C. Reaction progress was monitored using HPLC. The reaction was typically complete after 18 hours of agitation.

The general procedure was as follows. Equipped a three-necked round-bottomed flask in a cooling tub with a mechanical stirrer, nitrogen inlet, thermocouple probe and an addition funnel. Charged the flask with HF9 (1.0 eq) and Tetrahydrofuran (13 vol); stirred to give a light yellow clear solution. Cooled to approximately −15° C. (dry ice-methanol bath) and add a 1 M Sodium hydroxide solution in $H_2O$ (1.5 eq) dropwise in a thin stream over 60 minutes at −15° C. to −5° C. Removed the cooling and stirred over 18 hours at ambient temperature. Monitored the reaction progression by HPLC The reaction is complete when <2% of starting material remains. Divided the reaction mixture in half and poured each half onto ice cold water in two separatory funnels and adjusted to pH 5-6 with a 0.5N hydrochloric acid solution. Extracted each funnel twice with Ethyl acetate and combine the organic layers. Added sodium chloride solid to the aqueous layer, stirred for 10 minutes and extract with ethyl acetate. Combined all organic layers and washed each funnel with brine, dried over $MgSO_4$, added charcoal, filtered both organic mixtures, rinsed the filter twice with ethyl acetate. Concentrated the filtrates under vacuum to yield a light yellow solid. Triturated the crude compound with acetonitrile, filtered to collect the solids and rinsed twice with diethyl ether. Dry the product at ambient temperature overnight. The final cake wash can be performed with an equal volume of tert-butyl methyl ether (MTBE), and the final diethyl ether wash can be eliminated. The isolated HG0 cake, when wet with ACN, exhibited a high solubility in MTBE.

Starting from HF9, an isolated HG0 product (45% yield, 52.6% a/a by HPLC) was obtained. A hot (60° C.) trituration of the HG0 cake in EtOAc (300 mL), afforded HG0 (81.8% a/a). Significant gains in purity (e.g. 52.6% a/a to 81.6% a/a) were achieved when HG0 samples were re-slurried in EtOAc. Acquired data is presented in Table 11.

TABLE 11

Summary of manufactured HG0.

| HG0 Lot # | HF9 mass (g) | HG0 mass (%) | Yield (%) | HPLC purity (% a/a) |
|---|---|---|---|---|
| 047-1 | 4.7 | 2.34 | 51 | 89.9 |
| 087-1 | 45.0 | 18.9 | 45 | 52.6[A] |
| 089-1[B] | 45.0 | 10.0 | 24 | 57.0[C] |

[A] HG0 cake 087-1 was triturated in EtOAc (300 mL, 60° C.), filtered and afforded HG0 (81.8% a/a, 092-3).
[B] Concentration of the filtrate obtained after isolation of 087-1 afforded 10.0 g (24%, 57.0% a/a) of HG0 (089-1).
[C] HG0 cake 089-1 was re-slurried in EtOAc, filtered and afforded HG0 (69.7% a/a, 092-1).

Example 8

Coupling of Acid HG0 with HNPr2 to Afford Amide HG1

The amide preparation between acid HG0 and $HNPr_2$ was performed according to the following conditions: EDC, HOBt, DCM, −15° C. to 20-25° C. (Table 13).

The general procedure was as follows. Equipped a three-necked round-bottomed flask in a cooling tub with a mechanical stirrer, nitrogen inlet and thermocouple probe. Charged the flask with Dipropylamine (1.2 eq) and Dichloromethane (10 vol) and cooled the clear solution to −10° C. (dry ice-methanol bath). Added N-(3-dimethylaminopropyl)-N-ethylcarbodiimide.HCl (1.2 eq) followed by N,N-Diisopropylethylamine (1.3 eq) over 5 minutes at −15° C. and stirred the reaction mixture for 40 minutes between −15° C. to −5° C. Cooled to −15° C. and added HG0 (1.0 eq) followed by 1-Hydroxybenzotriazole monohydrate (1.2 eq) over 5 minutes, maintaining an internal temperature between −15° C. and −12° C. Remove the cooling and stir over 14 hours at ambient temperature. Monitored the reaction progression by HPLC. The reaction can be quenched when <1% of starting material remains. The product was isolated by pouring the reaction mixture onto water in separatory funnel and separating the organic layer. Extracted the aqueous layer with dichloromethane. Washed the combined organic layers with ice cold 0.5N hydrochloric acid solution two times. Back extracted the aqueous layers and washes twice with dichloromethane. Washed the combined organic layers twice with saturated sodium bicarbonate solution and once with brine. Combined the aqueous layers and washes and back extracted twice with dichloromethane. Washed this organic layer with brine. Combined all organic layers, dried over $MgSO_4$, added charcoal, filtered and rinsed twice with dichloromethane. Concentrated the filtrate under vacuum to yield a light yellow foamy/gummy solid on a rotary evaporator. Transferred the solids to a drying tray and dried the product at ambient temperature overnight under vacuum with a nitrogen bleed.

No solid precipitation was observed upon use of either diethyl ether or MTBE followed by cooling (−20° C., 12 hours, Ref % 1077-M-166).

Starting from 29.5 g of HG0 an isolated HG1 mass of 35.9 g (100% yield, 88.5% a/a by HPLC) was obtained. Acquired data is presented in Table 12.

TABLE 12

Summary of manufactured HG1.

| HG1 Lot # | HG0 mass (g) | HG1 mass (g) | Yield (%) | HPLC purity (% a/a) |
|---|---|---|---|---|
| 147-1 | 29.5 | 35.9 | 100 | 88.5 |
| 104-1 | 16.29 | 16.78 | Note A | 69.2 |
| 105-1 | 9.15 | 8.90 | Note A | 68.3 |

A HG1 lot#'s 104-1 & 105-1 exhibited low purities due to a polar impurity of ~20% a/a. Samples 104-1 and 105-1 where combined and purified by column chromatography on silica gel to afford HG1 of 91.3% a/a (Lot# 108-1).

The crude isolated purity of HG1 was 68-88% a/a, and the desired starting purity for the Suzuki coupling was >90% a/a. Substantial gains in purity could be gained by column chromatography or trituration (cyclohexane/DCM). Further purification of HG1 was demonstrated by two separate methods. Firstly, a 3.0 g sample of HG1 (88.5% a/a) was purified by column chromatography on silica gel (75 g, 70-230 mesh) using an increasing gradient of MTBE in DCM (0 to 50% v/v). Fraction elution was monitored (TLC) and single spot fractions were pooled and concentrated in vacuo to afford 2.4 g (80% recovery) of a pale yellow solid exhibiting a HPLC purity of 94.5% a/a. Secondly, a 13.0 g sample of HG1 (88.5% a/a) was purified by recrystallization from cyclohexane and heptanes (10:1, v/v) to afford a 9.5 g (73% recovery) of a foam having a HPLC purity of 92%. In this instance, the enriched HG1 is actually obtained upon concentration of the filtrate. The impurities are captured in the isolated cake.

Example 9

Suzuki Coupling of Aryl Bromide HG1 with Boronic Acid HG2 to Afford HG3, Depalladation of HG3, and N—BOC Deprotection of HG3 to Afford HG4

The Suzuki coupling of aryl bromide HG1 and boronic acid HG2 was performed according to the experimental conditions summarized as follows: HG1: 1 equiv, HG2: 1.2 equiv, $Pd(OAc)_2$: 0.025 equiv, ligand (4,4'-(Phenylphosphinidene)bis(benzenesulfonic acid) dipotassium salt hydrate): 0.05 equiv, $Na_2CO_3$: 3 equiv, EtOH: 10 volumes, reflux, 4 hours. Reaction progress was monitored using HPLC. The depalladation was performed using QUADRASIL™ AP (www.reaxa.com). The N—BOC-deprotection of HG3 to afford HG4 was performed according to the procedure below.

A 250 mL, 3-neck round bottom flask, was equipped with a mechanical stirrer, thermometer, gas-diffusion tube, and addition funnel. The flask was charged with HG1 (7.0 g) and ethanol (70 mL, anhydrous grade). The batch was agitated (40 min) to afford a clear solution while de-gassing with nitrogen. To the batch was charged $Pd(OAc)_2$ (86 mg, 0.025 equiv), ligand (377 mg, 0.05 equiv), HG2 (3.96 g, 1.2 equiv), and $Na_2CO_3$ (4.83 g, 3 equiv) while constantly degassing the batch medium for an additional 30 minutes. The yellow suspension was heated to reflux (75-78° C.) while monitoring for the consumption of HG1 by HPLC analysis (IPC 110-C, residual HG1 with respect to HG3: 1.9% after 4 hours). After 4 hours, the batch was cooled to ambient temperature and charged with Celite (1.4 g, 20% w/w with respect to HG1). The batch was further agitated (1 h, 20-25° C.) and filtered through a sintered glass funnel. The cake was washed with ethanol (2×7 mL, anhydrous grade). The ethanolic filtrate was reduced to 2 volumes using a rotary evaporator. The distillation residue was re-dissolved in ethyl acetate (14 ml) and reduced to 1 volume. The residue was re-dissolved in ethyl acetate (70 mL), agitated for 30 minutes (20-25° C.) and clarified by filtration to remove the lactam impurity. The cake was washed with ethyl acetate (2×7 mL). The collected filtrate was charged with QUADRASIL™ AP (350 mg), agitated (3 hours, 20-25° C.), and filtered through a sintered glass funnel. The collected cake was rinsed with ethyl acetate (2×7 mL). The filtrate was sampled to determine residual palladium (192-1). The filtrate was concentrated to 1 volume (7 mL) and re-dissolved in cyclohexane (35 mL). The batch was concentrated to 1 volume (7 mL) and re-dissolved in dichloromethane (50 mL). The brown solution was cooled to −20 to −25° C. A solution of trifluoroacetic acid (14.2 g, 10 equiv) in DCM (20 mL) was added to the batch over 30 minutes while maintaining the internal temperature in the range of −20 to −25° C. The batch was allowed to warm to 20-25° C. overnight, without removal of the cooling bath. The batch was sampled for IPC (Residual HG3 with respect to HG4). The batch was charged into water (150 mL, 5° C.), agitated (15 min) and the phases were separated. The aqueous phase was back extracted with DCM (30 mL). The combined DCM extracts were basified with 10% $NaHCO_3$ solution (4×60 mL, 10 min of agitation for each wash). The combined aqueous was back extracted with DCM (30 mL). The combined DCM layers were washed with brine (60 mL), dried ($Na_2SO_4$, 1.5 g) and concentrated to 1 volume (with respect to HG1) on a rotary evaporator. The residue (pink slurry) was triturated with ethyl acetate (28 mL, 2 hours, 20-25° C.), filtered and rinsed with ethyl acetate (2×4 mL) and heptanes (2×4 mL). The HG4 cake was dried under reduced pressure. This effort afforded 2.15 g (95.6% a/a lot #193-1) of HG4. The HG4 sample was triturated (2 h, 20-25° C.) in DCM (5 mL) and ethyl acetate (20 mL), filtered and dried under reduced pressure to afford 1.85 g (29% yield, 97.35% a/a, lot #193-2).

A further HG4 purification strategy was developed using a 10 mL DCM solution of crude HG4 (derived from 2.5 g of HG1, 74.9% a/a lot #190-1), which had been processed through a typical aqueous work-up. Cyclohexane (30 mL) was charged (20-25° C.) and the suspension agitated for a further 1 hour. The resulting pink suspension was filtered and rinsed with cyclohexane (5 mL). The isolated cake (1.15 g, lot #196-1) exhibited a purity of 95.9% a/a. A 20 mg sample of cake 196-1 was further triturated in EtOAc (1 mL, 1 h, 20-25° C.) and filtered. The isolated solid (196-2) exhibited a purity of 99.7% a/a. After review of the HPLC purity results from cake 196-2, the remaining 1.1 g of cake 196-1 was triturated in EtOAc (10 mL, 16 h, 20-25° C.). The suspension was filtered and the isolated cake was washed with EtOAc (2 mL) and cyclohexane (2 mL). The HG4 sample was dried overnight in a vacuum oven at 40° C. to afford 0.95 g (51% yield from HG1, lot #196-3) of HG4. Analysis by HPLC revealed a final purity of 99.36% a/a.

Table 13 provides a summary of the preparation of HG3 using differing reaction conditions. The main impurity in the crude reaction mixture as identified by LC MS was the hydrolysis product of the amidine (referred to herein as "the lactam" or "the lactam impurity"). The lactam (RRt 1.02, M+460) was present in of the crude reaction mixtures ranging from 15-25% a/a. Two methods of controlling the level of lactam impurity in the crude HG3 product are suitable. First, the lactam can be partially precipitated from the crude HG3 product using a trituration in ethyl acetate (30 min, 20-25° C.) and removed by filtration. Secondly, the formation of the lactam can be controlled during the Suzuki coupling if the reaction and work-up conditions are kept largely anhydrous. Therefore, lower levels of lactam (5-10% a/a vs. 15-25% a/a) where observed if the Suzuki was performed in ethanol (10 volumes) only.

TABLE 13

Summary of attempted Suzuki coupling conditions of HG1 and HG2 to afford desired product HG3.

| Reaction Reference | Reaction Conditions | Reaction Scale | Outcome |
|---|---|---|---|
| 052-1 | 5% Pd/C from Johnson Matthey (Type A5030232-5), $K_3PO_4$, EtOH/$H_2O$ (20-25 to 80° C.) | 0.1 g | Complex mixture (HPLC), with <1% a/a of HG3. |
| 052-2 | 5% Pd/C from Johnson Matthey (Type A570129-5), $K_3PO_4$, EtOH/$H_2O$ (20-25 to 80° C.) | 0.1 g | Complex mixture (HPLC), with <1% a/a of HG3. |
| 052-3 | 5% Pd/C from Johnson Matthey (Type A102023-5), $K_3PO_4$, EtOH/$H_2O$ (20-25 to 80° C.) | 0.1 g | Complex mixture (HPLC), with <1% a/a of HG3. |
| 052-4 | 5% Pd/C from Johnson Matthey (lot# C-7712), $K_3PO_4$, EtOH/$H_2O$ (20-25 to 80° C.) | 0.1 g | Complex mixture (HPLC), with <1% a/a of HG3. |
| 052-5 | 5% Pd/C from Johnson Matthey (Type A50308-5), $K_3PO_4$, EtOH/$H_2O$ (20-25 to 80° C.) | 0.1 g | Complex mixture (HPLC), with <1% a/a of |
| 054 | $Pd(OAc)_2$, ligand[4], $Na_2CO_3$, EtOH, $H_2O$, 80-85° C. | 0.1 g | Complete reaction conversion after 1 hour at reflux. Batch residue was purified by column chromatography to provide analytical standard of HG3. |
| 055-1 | $Pd(OAc)_2$, $Bu_4NOAc$, $K_2CO_3$, EtOAc, 85° C. | 0.1 g | Complex mixture (HPLC), with <1% a/a of HG3 |
| 055-2 | $Pd(OAc)_2$, $Bu_4NOAc$, $K_2CO_3$, IPAC, 85° C. | 0.1 g | Complex mixture (HPLC), with <1% a/a of HG3 |
| 059-1 | Pd-EnCat 30, $K_2CO_3$, EtOH/$H_2O$, 80° C. | 0.25 g | 5% a/a of HG3 after overnight heating at 80-85° C. |

TABLE 13-continued

Summary of attempted Suzuki coupling conditions of HG1 and HG2 to afford desired product HG3.

| Reaction Reference | Reaction Conditions | Reaction Scale | Outcome |
|---|---|---|---|
| 059-2 | Pd-EnCat 30, $K_3PO_4$, EtOH/$H_2O$, 80° C. | 0.25 g | 9% a/a of HG3 after overnight heating at 80-85° C. |
| 060-1 | 5% Pd/C from Johnson Matthey (Type A5030232-5), $K_3PO_4$, EtOH/$H_2O$, 80° C. | 0.25 g | Complex mixture (HPLC), with <1% a/a of HG3 |
| 060-2 | 5% Pd/C from Johnson Matthey (Type A5030232-5), $K_2CO_3$, EtOH/$H_2O$, 80° C. | 0.25 g | Complex mixture (HPLC), with <1% a/a of HG3 |
| 064-1 | Pd-EnCat 30, $K_2CO_3$, IPA/$H_2O$, 80° C. | 0.25 g | 41% complete after 24 hours. Other impurities formed. |
| 064-2 | Pd-EnCat 40, $K_2CO_3$, IPA/$H_2O$, 80° C. | 0.25 g | No reaction observed after 24 hours. |
| 065-1 | Pd-EnCat Poly TPP30, $K_3PO_4$, IPA/$H_2O$, 80° C. | 0.25 g | 40% complete after 24 hours. Other impurities formed. |
| 065-2 | Pd-EnCat TPP30, $K_2CO_3$, IPA/$H_2O$, 80° C. | 0.25 g | 2% complete after 24 hours. Other impurities formed. |
| 065-3 | Pd-EnCat Poly 30 NP, $K_3PO_4$, IPA/$H_2O$, 80° C. IPA/$H_2O$ | 0.25 g | 19% complete after 24 hours. Other impurities formed. |
| 068-1 | Pd-EnCat 30, $Bu_4NOAc$, Toluene 80° C., 24 hour | 0.25 g | ~10-15% complete. Many other impurities formed as observed by TLC |
| 068-2 | Pd-EnCat 30, $Bu_4NOAc$, ACN 80° C., 24 hour | 0.25 g | ~10-15% complete. Many other impurities formed as observed by TLC |
| 068-3 | Pd-EnCat 30, $Bu_4NOAc$, IPA 80° C., 24 hour | 0.25 g | HPLC: ~1% a/a of HG1 remaining |
| 072 | $Pd(OAc)_2$, ligand[4], $Na_2CO_3$, EtOH, $H_2O$, 80-85° C. | 1.00 g | Consumption of HG1 completed after 24 hours. 59.5% a/a of HG3. 21.4% a/a of lactam. |
| 073 | Pd-EnCat 30, $Bu_4NOAc$, IPA 80° C., 24 hour, over-head agitation | 1.00 g | 8.6% a/a of HG3 after 18 hours of heating. Over-head agitation did not grind encapsulated Pd as well as magnetic agitation. |
| 084-1 | $Pd(OAc)_2$, ligand[4], $Bu_4NOAc$, $K_2CO_3$, EtOAc, 80-85° C. | 0.1 g | No product observed after 24 hours of heating at reflux. |
| 084-2 | $Pd(OAc)_2$, ligand[4], $Bu_4NOAc$, $K_2CO_3$, IPAC, 80-85° C. | 0.1 g | No product observed after 24 hours of heating at reflux. |
| 178 | $Pd(OAc)_2$, ligand[4], $Na_2CO_3$, EtOH, 80-85° C. (Anhydrous Suzuki) | 2.28 g | Afforded 1.52 g of HG3 (51.4% a/a) containing lactam (14.3% a/a). HG1 consumed after 4 hours at reflux. |
| 184 | $Pd(OAc)_2$, ligand[4], $Na_2CO_3$, EtOH, 80-85° C. (Anhydrous Suzuki) | 5.0 g | IPC at 4 hours: HG3, 65.42% a/a; lactam, 10.75% a/a and HG1, 0.17% a/a. Batch mixture used to define both lactam and Pd removal strategies. |
| 191 | $Pd(OAc)_2$, ligand[4], $Na_2CO_3$, EtOH, 80-85° C. (Anhydrous Suzuki) | 7.0 g | IPC at 4 hours: HG3, 64.00% a/a; lactam, 4.79% a/a and HG1, 1.23% a/a. Batch solvent was exchanged from EtOH to EtOAc. Batch filtered to remove lactam. |

Notes:
[4]Ligand: 4,4'-(Phenylphosphinidene)bis(benzenesulfonic acid) dipotassium salt hydrate, (CAS # 308103-66-4, Sigma-Aldrich product # 479497).

Example 10

Depalladation of Suzuki Product HG3

A successful depalladation can be completed during the non-aqueous work-up of the Suzuki batch mixture. Either a treatment of the clarified (Celite, filtration) ethanolic HG3 batch mixture or treatment after the solvent exchange from ethanol to ethyl acetate with an appropriate Pd-scavenger provides satisfactory results.

Upon completion of a successful Suzuki coupling performed in ethanol (5.0 g of HG1, Exp. #184) the crude HG3 batch mixture was clarified by filtration through Celite. The resulting ethanolic HG3 filtrate was diluted to a final volume of 200 mL (25 mg/mL) and divided into two portions of 100 mL each. One portion was further subdivided into 4 mL aliquots and treated as outlined in Table 14. The completed trials were filtered (0.5 pm PTFE filter) and the filtrate analyzed for residual palladium content (using ICP-OES).

TABLE 14

Selection of Pd-scavengers used to treat HG3 ethanolic solution following Suzuki coupling.

| Pd Scavenger | Dose (mg/mL) | Vol (mL) | Stir Time (h) | Temp (° C.) | Reference (Lot#) | Pd (ppm) |
|---|---|---|---|---|---|---|
| QUADRAPURE ™ IDA | 50 | 4 | 4 | 20-25 | 186-1 | 176 |
| QUADRAPURE ™ BZA | 50 | 4 | 4 | 20-25 | 186-2 | 41 |

TABLE 14-continued

Selection of Pd-scavengers used to treat HG3 ethanolic solution following Suzuki coupling.

| Pd Scavenger | Dose (mg/mL) | Vol (mL) | Stir Time (h) | Temp (° C.) | Reference (Lot#) | Pd (ppm) |
|---|---|---|---|---|---|---|
| QUADRAPURE ™ AMPA | 50 | 4 | 4 | 20-25 | 186-3 | 168 |
| QUADRAPURE ™ TU | 50 | 4 | 4 | 20-25 | 186-4 | 146 |
| QUADRAPURE ™ C | 50 | 4 | 4 | 20-25 | 186-5 | 17 |
| QUADRASIL ™ MTU | 50 | 4 | 4 | 20-25 | 186-6 | 212 |
| QUADRASIL ™ MP | 50 | 4 | 4 | 20-25 | 186-7 | 25 |
| QUADRASIL ™ AP | 50 | 4 | 4 | 20-25 | 186-8 | 10 |
| QUADRASIL ™ TA | 50 | 4 | 4 | 20-25 | 186-9 | 64 |
| DARCO ® KB-G | 50 | 4 | 4 | 20-25 | 186-10 | 11 |
| Control | N/A | 4 | 4 | 20-25 | 186-11 | 174 |

Note:
N/A = Not applicable

From Table 14, acceptable Pd results were obtained with QUADRAPURE™ C, QUADRASIL™ AP and DARCO® KB-G (available from Norit Americas, Inc.). However, further analysis of successful samples using HPLC showed that the HG3 sample which was treated with DARCO® KB-G (lot #186-10) had suffered from complete degradation. Therefore, this study highlighted two scavenger options that could be used to successfully treat the ethanolic HG3 solution.

The second approach was to treat the HG3/ethyl acetate product stream with an identical selection of scavengers. This was accomplished by first subjecting a 50 mL aliquot of the second ethanolic portion of HG3 to a solvent exchange (rotovap) from ethanol into ethyl acetate. The final ethyl acetate volume was adjusted to 50 mL. This solution was clarified, subdivided into 4 mL aliquots and treated as outlined in Table 15. The completed trials were filtered (0.5 pm PTFE filter) and the filtrate analyzed for residual palladium content.

TABLE 15

Selection of Pd-scavengers used to treat HG3/ethyl acetate solution following Suzuki coupling/solvent exchange from ethanol.

| Pd Scavenger | Dose (mg/mL) | Vol (mL) | StirTime (h) | Temp (° C.) | Reference (Lot#) | Pd (ppm) |
|---|---|---|---|---|---|---|
| QUADRAPURE ™ IDA | 50 | 4 | 4 | 20-25 | 187-1 | 80 |
| QUADRAPURE ™ BZA | 50 | 4 | 4 | 20-25 | 187-2 | 19 |
| QUADRAPURE ™ AMPA | 50 | 4 | 4 | 20-25 | 187-3 | 61 |
| QUADRAPURE ™ TU | 50 | 4 | 4 | 20-25 | 187-4 | 12 |
| QUADRAPURE ™ C | 50 | 4 | 4 | 20-25 | 187-5 | 102 |
| QUADRASIL ™ MTU | 50 | 4 | 4 | 20-25 | 187-6 | 3 |
| QUADRASIL ™ MP | 50 | 4 | 4 | 20-25 | 187-7 | <1 |
| QUADRASIL ™ AP | 50 | 4 | 4 | 20-25 | 187-8 | 4 |
| QUADRASIL ™ TA | 50 | 4 | 4 | 20-25 | 187-9 | 2 |
| DARCO ® KB-G | 50 | 4 | 4 | 20-25 | 187-10 | 12 |
| Control | N/A | 4 | 4 | 20-25 | 187-11 | 90 |

Note:
N/A = Not applicable

From Table 15, acceptable Pd results were obtained with QUADRAPURE™ TU, QUADRASIL™ MTU, QUADRASIL™ MP, QUADRASIL™ AP, QUADRASIL™ TA and DARCO® KB-G. As observed previously, analysis of the Darco IU3-G (lot #187-10) treated sample for HPLC purity identified that the sample had completely degraded. Therefore, this study highlighted five scavenger options that could be used to successfully treat the HG3 solution in ethyl acetate.

Palladium removal from the Suzuki batch mixture can be conveniently performed in either EtOH or ethyl acetate. Also, this process can be completed with 1 treatment in a relatively short period of time.

Example 11

N—BOC Deprotection of HG3 to Afford Target HG4

Removal of the N—BOC protecting group was accomplished using trifluoroacetic acid (TFA, 10 equiv) in DCM (15 volumes, −25 to 25° C., 24 hours) according to the following procedure. A solution of TFA was prepared in an equal volume of DCM and added to a cold (−25° C.) solution of HG3 over a period of 1 hour, while maintaining the batch temperature <20° C. Upon completion of the addition, the temperature of the batch was allowed to rise to 20-25° C. The completed reaction mixture was diluted into cold (0-5° C.) water. After a phase separation and back extraction of the aqueous layer, the pH of the batch was adjusted with 10% NaHCO$_3$ solution to remove the excess TFA. The organic phase was further washed with brine, dried (MgSO$_4$), filtered and concentrated to a light yellow slurry. The slurry was triturated in EtOAc (11.6 volumes, 2 hours, 20-25° C.) and filtered to afford a light pink solid. The cake was washed with EtOAc (2 portions of 1.5 volume each) and final wash with heptanes (2 portions of 1.5 volume each). The final compound was dried in a vacuum oven (40° C., 48 hours).

The deprotection of HG3 was performed using this procedure. The reaction progress was monitored using HPLC. A representative deprotection was performed on HG3 (560 mg, 1 mmol, 74.9% a/a). From this trial was isolated 320 mg (92.3% yield) of HG4 (98.6% a/a).

For these experiments, the batch volume was reduced to approximately 1 volume of DCM with respect to HG1, prior to the addition of ethyl acetate to precipitate the HG4 product.

Example 12

Preparation of HG4

The Suzuki coupling and deprotection steps were carried out on a 7.0 g scale of HG1 (91.25% a/a). The Suzuki coupling was performed under the following anhydrous conditions: 1 equiv HG1, 1.2 equiv HG2, 0.025 equiv Pd(OAc)$_2$, 0.05 equiv ligand (4,4'-(Phenylphosphinidene)bis(benzenesulfonic acid) dipotassium salt hydrate), 3 equiv Na$_2$CO$_3$, 10 volumes EtOH, 75-78° C., 4 hours. The residual HG1 with respect to HG3 after 4 hours of heating at reflux was 1.9%. The cooled Suzuki batch mixture was charged with Celite (20% w/w with respect to HG1), agitated and filtered. The ethanolic solution of HG3 was subjected to a solvent exchange from ethanol to ethyl acetate (final volume: 70 mL). This process precipitated the lactam impurity derived from HG3. The batch was filtered to remove the lactam impurity.

The ethyl acetate filtrate containing HG3 was treated with QUADRASIL™ AP (350 mg, 3 h, 20-25° C.) and filtered. The filtrate volume was reduced to about 1 volume with respect to HG1, and the concentrate diluted in cyclohexane (5 volumes) and reduced again to about 1 volume with respect to HG1. The outcome of this process was a solution of HG3 (55.6% a/a) in approximately 1 volume of cyclohexane, which had not been subjected to an aqueous work-up or semi-purification by column chromatography. This HG3 solution was taken forward into the deprotection step as outlined in Example 11. Following the basification and aqueous work-up, the volume of the batch was reduced to about 1 volume of DCM with respect to HG1. The HG4 product was precipitated with EtOAc (4 volumes, 2 hours, 20-25° C.). The product was collected by filtration and washed with EtOAc (8 mL) and heptanes (8 mL). This process afforded 2.15 g (34% yield) of HG4, which exhibited an HPLC purity of 95.6% a/a. This sample was further triturated with DCM/EtOAc (1:4, 25 mL, 2 h). Re-isolation afforded 1.85 g (29% yield) of HG4, which exhibited an HPLC purity of 97.3% a/a.

In order to obtain HG4 with a purity of >98%, further crystallizations were performed (Table 16). Four different solvent systems were assayed with particular emphasis on examining the filtrate for impurity content and product losses. The best results were obtained using cyclohexane as the anti-solvent, because this filtrate contained the lowest observed levels of HG4 and highest levels of combined impurities. This purification method was assessed on a 10 mL DCM solution of crude HG4 (derived from 2.5 g of HG1, 74.9% a/a), which had been processed through a typical aqueous work-up. Cyclohexane (30 mL) was charged (20-25° C.) and the suspension agitated for a further 1 hour. The resulting pink suspension was filtered and rinsed with cyclohexane (5 mL). The isolated cake (1.15 g) exhibited a purity of 95.9% a/a. A 20 mg sample of cake 196-1 was further triturated in EtOAc (1 mL, 1 h, 20-25° C.) and filtered. The isolated solid exhibited a purity of 99.7% a/a by HPLC. After review of the HPLC purity results from cake 196-2, the remaining 1.1 g of cake 196-1 was triturated in EtOAc (10 mL, 16 h, 20-25° C.). The suspension was filtered and the isolated cake was washed with EtOAc (2 mL) and cyclohexane (2 mL). The HG4 sample was dried overnight in a vacuum oven at 40° C. to afford 0.95 g (51% yield from HG1) of HG4. Analysis by HPLC revealed a final purity of 99.36% a/a.

TABLE 16

HGR crystallization study on lot# 193-2 (97.3% a/a).[A]

| Solvent mixtures screened | Solvent composition | Observation | Observed HG4 in mother liquor (% a/a)[B, C] |
|---|---|---|---|
| DCM/EtOAc | 1:8 | Crystallization | 82.44 |
| DCM/MTBE | 1:4 | Crystallization | 68.66 |
| DCM/Cyclohexane | 1:2.5 | Crystallization | 28.73 |
| DCM/Heptane | 1:2 | Oiled out | 36.33 |

Notes:
[A]50 mg of HG4 was dissolved in DCM (200 µL) and then the anti-solvent was added into the trial with agitation. The resulting HG4 cakes were filtered off and the filtrate analyzed by HPLC.
[B]HPLC analysis was acquired using the generic HPLC method as outlined in the Appendix.
[C]All other impurities = 100 - HG4% a/a.

Example 13

Preparation of HG4

The Suzuki coupling and deprotection steps were carried out again, based on 6.1 g scale of HG1 (92.7% a/a). The Suzuki coupling was again performed under anhydrous conditions (HG1: 1 equiv, HG2: 1.2 equiv, Pd(OAc)$_2$: 0.025 equiv, ligand (4,4'-(Phenylphosphinidene)bis(benzenesulfonic acid) dipotassium salt hydrate): 0.05 equiv, Na$_2$CO$_3$: 3 equiv, EtOH: 10 volumes, 75-78° C., 4-6 hours). After 6 hours of heating at reflux HG1 was not detected by HPLC. The cooled Suzuki batch mixture was charged with Hyflo SuperCel NF (20% w/w with respect to HG1), agitated and filtered. The ethanolic solution of HG3 was subjected to a solvent exchange from ethanol to ethyl acetate (final volume: 60 mL). Analysis ($^1$H NMR) of the resulting HG3 solution in ethyl acetate did not detect ethanol in the batch. The batch was filtered at this stage and the collected cake was analyzed by HPLC and found to be primarily composed of HG2 (50% a/a), HG3 (14% a/a) and the lactam impurity (6% a/a).

The ethyl acetate filtrate containing HG3 was sequentially treated with QUADRASIL™ AP as shown in Table 17. The initial palladium level was measured at 364 ppm in solution. This was extrapolated to 5700 ppm in the solid. A final QUADRASIL™ charge of 650% w/w with respect to HG1 was employed in the effort.

TABLE 17

Summary of Pd scavenging efforts on HG3 lot# 119-4 with QUADRASIL ™ AP

| Sample Ref # | QUADRASIL ™ AP (g) | % w/w | Agitation time (h) | Sample type | Residual Pd (ppm) |
|---|---|---|---|---|---|
| 120-1 | 0 | 0 | -:- | Solution | 364 |
| 120-2 | 3.0 | 50 | 1 | Solution | 163 |
| 120-4 | 3.0 | 100 | 1 | Solution | 78 |
| 121-1 | 3.0 | 150 | 1 | Solution | 43 |
| 121-3 | 3.0 | 200 | 1 | Solution | 32 |
| 122-1 | 3.0 | 250 | 1 | Solution | 18 |
| 122-3 | -:- | 250 | | Solid | 277 |
| 124-1 | 6.0 | 350 | 16 | Solid | 127 |
| 125-1 | 6.0 | 450 | 16 | Solid | 65 |
| 127-1 | 12.0 | 650 | 16 | Solid | 44 |

Note:
Solid samples were obtained by concentrating aliquots of the HG3/EtOAc filtrate.

Before running the deprotection step a $^1$H NMR (DMSO-d$_6$) assay of HG3 using an internal standard revealed 1.94 g of HG3 in the treated process stream (lot #127-2). This solution was subjected to a solvent exchange into DCM by first concentrating (rotovap) down to about 1 volume. The batch was charged with cyclohexane (50 mL) and agitated. The resulting solution was reconcentrated to about 1 volume. The batch was re-slurried in a second portion of cyclohexane (50 mL) and reconcentrated to a residue (3.7 g). This material was redissolved in DCM (37 mL) and treated with TFA. The final IPC chromatogram (HPLC) revealed that the residual 1-103 (1.2% a/a) with respect to HG4 (87.1% a/a) was 1.4%. The batch was subjected to a typical aqueous work-up, and clarification through Whatman paper. The collected filtrate was concentrated to a final volume of 10 mL. The crude HG4 product was precipitated using cyclohexane (36 mL) and the batch was further agitated for 1 hour. The HG4 product was collected by filtration and the cake was washed with cyclohexane (12 mL). This effort afforded 1.65 g (106% yield, wet) of HG4 (98.2% a/a by HPLC, lot #133-1). The entire cake was triturated in ethyl acetate (10 volumes, 16 h, 20-25° C.) and collected by filtration.

The cake was washed with ethyl acetate (12 mL), cyclohexane (12 mL) and heptanes (16 mL). This effort afforded 1.31 g of HG4 (lot #135-1). A sample (200 mg) of this material was removed for preliminary testing and the remainder subjected to oven drying. The HPLC purity of lot #135-1 was 96.7% a/a and the level of residual palladium was determined to be 44 ppm. Therefore, we observed no attrition of palladium during the deprotection step. The final HG4 sample was dried in a vacuum oven (−28 to −29 inches Hg) while incorporating a nitrogen bleed through the oven. The drying progress was followed by $^1$H NMR. The sample was dried for an initial 48 hours at 40° C. The temperature was ramped up to 50° C. for a further 48 hours and a further analysis revealed that the sample contained 3.3% w/w of ethyl acetate. The oven temperature was increased to 60-62° C. and the sample was dried for a further 72 hours. A final analysis (NMR) revealed that the residual ethyl acetate level had fallen to 0.46% w/w. Thus, the dried HG4 sample (0.99 g, 64% yield, lot #140-1) was submitted for final product testing (HPLC purity, residual TFA, residual solvents, see Table 18). An HPLC purity of 98.7% a/a was obtained with only one impurity (RRt 1.13) greater than <0.5% a/a.

Final product testing was performed on HG4 in parallel with a sample manufactured using Si-Thiol (i.e., silica 1-propanethiol, 2% w/w, DCM, 20-25° C.) as a palladium scavenger. The Si-Thiol was added in three portions, with a 6 hour period of agitation after each addition. A final charge of charcoal (10% w/w, 10 min agitation) and filtration completed the process. The Si-Thiol purified sample (378-15) was tested in parallel and exhibited a purity of 98.0% a/a. Both samples exhibited a very similar impurity profile and contained the RRt 1.13 impurity at the same level (0.6% a/a). The residual TFA limit was determined to be trace (<500 ppm) in the 140-1 material and all residual solvents were found to be below ICH guideline values. There was insufficient quantity of lot #378-15 to perform testing for residual TFA and residual solvents. Overall, by this method, a 1 g sample of HG4 (lot #140-1) was prepared in an approximate 23% yield from HG1. The final HG4 sample exhibited an HPLC purity of 98.7% a/a with only one impurity resting outside of <0.5% a/a. This impurity is hypothesized to be the lactam impurity derived from HG3. Analytical testing showed that both the residual TFA and residual solvent limits were satisfied. The residual palladium level rested at 44 ppm. Characterization data are presented in Table 18.

TABLE 18

Product testing of HG4 samples using two methods for purification

| Test | Method | HG4 Samples QUADRASIL ™ AP purified Lot# 140-1 | Si-Thiol purified Lot#378-15 |
|---|---|---|---|
| Appearance | Visual | Beige solid | Pink solid |
| Proton NMR | NMR | Conforms | Conforms |
| Purity, HPLC (% a/a) | HPLC$^4$ | HG4: 98.7% a/a | HG4: 98.0% a/a |
| | | RRT 0.89: 0.14% a/a | RRT 0.895: 0.23% a/a |
| | | RRT 0.94: 0.09% a/a | RRT 0.94: 0.06% a/a |
| | | RRT 0.96: 0.05% a/a | RRT 0.96: 0.04% a/a |
| | | RRT 0.98: 0.13% a/a | RRT 0.98: 0.06% a/a |
| | | RRT 1.02: 0.06% a/a | RRT 1.03: 0.11% a/a |
| | | RRT 1.03: 0.02% a/a | RRT 1.06: 0.04% a/a |
| | | RRT 1.06: 0.03% a/a | RRT 1.07: 0.13% a/a |
| | | RRT 1.07: 0.01% a/a | RRT 1.09: 0.58% a/a |
| | | RRT 1.08: 0.16% a/a | RRT 1.13: 0.61% a/a |
| | | RRT 1.13: 0.60% a/a | No other impurity peaks >0.1% |
| | | No other impurity peaks >0.1% | |
| TFA content (% w/w) | Karl Fischer (USP) | Trace, <500 ppm | Not determined |
| Residual Pd (ppm) | ICP OES | 44 pm | 152 ppm |
| Residual solvents (% w/w) | Residual Solvents by Headspace GC | EtOH: not detected, <0.05% w/w EtOAc: 0.489% w/w DCM: not detected, <0.006% w/w Cyclohexane: trace, <0.04% w/w Heptanes: not detected, 0.05% w/w | Not determined |

TABLE 18-continued

Note A: HPLC Method
Method ID: 1506
Instrumentation: Waters
Column: Phenomenex, Gemini, C18
4.6 × 150 mm, 5 μm
Detector: 254 nm
Column temperature: ambient
Flow rate: 1.5 mL/min
Mobile Phase A: Water:CAN:Perchloric acid (950:50:2)
Mobile Phase B: ACN
Run Time: 30 min
Injection volume: 5 μL
Gradient Table

| Time | % A | % B |
|------|-----|-----|
| 0.00 | 90 | 10 |
| 15.00 | 10 | 90 |
| 20.00 | 10 | 90 |
| 20.10 | 90 | 10 |
| 30.00 | 90 | 10 |

Example 12

Further Examples of the Cross-Coupling Reaction

HG1 (1 eq.) was reacted with HG2 (1.2 eq), palladium on carbon (10% 0.10% eq), and sodium carbonate(3 eq) in methanol:water at 65° C. on 1 g scale. HPLC reaction check indicate no reaction after several hours reflux.

HG1 (1 eq.) was reacted with HG2 (1.3 eq), palladium acetate (0.10 eq), 4,4'(phenylphosphinidene)bisbenzenesulfonic acid dipotassium salt hydrate (0.20 eq) and sodium carbonate (3 eq) in water and ethanol at 60° C.-65° C. over one hour on 5.0 g scale and isolated 6.0 g of HG3 (Lot 26-1, yield 100%, HPLC: indicate 83% of product and another 13% of known lactam impurity). $^1$H-NMR confirmed the structure.

HG1 (1 eq.) was reacted with HG2 (1.3 eq), palladium acetate (0.05 eq), 4,4'(phenylphosphinidene)bisbenzenesulfonic acid dipotassium salt hydrate (0.10 eq) and sodium carbonate (3 eq) in water and NMP at 60° C.-65° C. over one hour on 1.0 g scale and followed by another 5 g scale. Isolated 7.0 g of crude HG3 (Lot 26-1, yield 97%, HPLC: indicates 82% of product and another 9.6% of known lactam impurity). $^1$H-NMR confirmed the structure.

HG1 (1 eq.) was reacted with HG2 (1.2 eq), palladium acetate (0.10 eq), tetrakis (hydroxymethyl) phosphonium sulfate (0.20 eq) and sodium carbonate (3 eq) in Ethanol:water at 65° C. on 1 g scale. HPLC reaction checks indicate no reaction after several hours of reflux.

HG1 (1 eq.) was reacted with HG2 (1.2 eq), palladium acetate (0.025 eq), 4,4'(phenylphosphinidene)bisbenzenesulfonic acid dipotassium salt hydrate (0.05 eq) and sodium carbonate (3.0 eq) in water (8 vol) and ethanol (20 vol) at 70° C.-75° C. This was performed on 10 g scale and followed by 100 g scale. Isolated 130 g of crude HG3 (Lot 38-1, 98% yield, HPLC: 87.0% and $^1$H-NMR confirmed the structure).

Further cross-coupling reactions were carried out using Pd(OAc)$_2$ (12 g, 0.054 mol, 0.1 eq), and 4,4'(phenylphosphinidene)bisbenzenesulfonic acid dipotassium salt hydrate (3 g, 0.006 mol, 0.01 eq.). Yields of HG3: 38-43%, with 91-92% purity.

Further cross-coupling reactions were carried out using Pd(OAc)$_2$ (19 g, 0.05 eq.), and 4,4'(phenylphosphinidene) bisbenzenesulfonic acid dipotassium salt hydrate (43 g, 0.05 eq.). Yield of HG3: 49% after column chromatography, with 88% purity.

What is claimed is:

1. A composition comprising {2-amino-8-[4-(pyrrolidinylcarbonyl)phenyl]-(3H-benzo[f]azepin-4-yl)}-N,N-dipropylcarboxamide and one or more palladium-containing contaminants, wherein the palladium is present in a concentration of less than 20 ppm by ICP-OES.

2. The composition of claim 1, wherein the palladium is present in a concentration of less than 15 ppm.

3. The composition of claim 1, wherein the {2-amino-8-[4-(pyrrolidinylcarbonyl)phenyl]-(3H-benzo [f]azepin-4-yl)}-N,N-dipropylcarboxamide is prepared using a palladium-catalyzed coupling reaction.

4. A method for preparing a composition of claim 1 comprising {2-amino-8-[4-(pyrrolidinylcarbonyl)phenyl]-(3H-benzo azepin-4-yl)}-N,N-dipropylcarboxamide, the method comprising: (a) purifying a solution of (tert-butoxy)-N-{4-(N,N-dipropylcarbamoyl)-8-[4-(pyrrolidinylcarbonyl)phenyl](3H-benzo [f]azepin-2-yl)}carboxamide by admixing the solution with a palladium scavenger; and (b) reacting the (tert-butoxy)-N-{4-(N,N-dipropylcarbamoyl)-8-[4- (pyrrolidinylcarbonyl)phenyl](3H-benzo[f]azepin-2-yl)}carboxamide with a protecting-group removal agent to provide {2-amino-8-[4-(pyrrolidinylcarbonyl)phenyl]-(3H-benzo[f]azepin-4-yl)}-N,N-dipropylcarboxamide, wherein the palladium scavenger is selected from: (i) silica beads functionalized with a functional group selected from —(CH$_2$)$_3$—NH$_2$, —(CH$_2$)$_3$—SH, —(CH$_2$)$_3$—NH—C(=S)—NHMe, and —(CH$_2$)$_3$—NH—(CH$_2$)$_2$—NH—(CH$_2$)$_2$—NH$_2$; (ii) polystyrene beads functionalized with a functional group selected from —CH$_2$—NH—C(=S)—NH$_2$ and —C$_6$H$_4$—CH$_2$—NH$_2$; and (iii) porous carbon particles having a surface area of at least about 1200 m$^2$/g, an average pore diameter of about 1 nm, and a particle diameter of about 0.3 mm to about 0.8 mm.

5. The method of claim 4, wherein the solution of (tert-butoxy)-N-{4-(N,N-dipropylcarbamoyl)-8-[4-(pyrrolidinylcarbonyl)phenyl](3H-benzo[f]azepin-2-yl)}carboxamide is prepared by contacting {2-[(tert-butoxy)carbonylamino]-8-bromo-(3H-benzo[f]azepin-4-yl]-N,N-dipropylcarboxamide with 4-pyrrolidinylcarbonylphenylboronic acid in the presence of a palladium catalyst and optionally in the presence of a ligand, wherein the contacting is carried out in a solvent and under substantially anhydrous conditions.

6. The method of claim 5, wherein the optional ligand is present and is 4,4'-(phenylphosphinidene)bis(benzenesulfonic acid) dipotassium salt hydrate.

7. The method of claim 5, wherein the solvent is ethanol, the base is sodium carbonate, and the catalyst is palladium (II) acetate.

8. The method of claim 5, wherein {2-[(tert-butoxy)carbonylamino]-8-bromo-(3H-benzo[f]azepin-4-yl)}-N,N-dipropylcarboxamide is prepared by contacting 2-[(tert-butoxy)carbonylamino]-8-bromo-3H-benzo[f]azepin-4-carboxylic acid with diisopropylamine in the presence of 1-ethyl-3-[3-dimethylaminopropyl]carbodiimide hydrochloride and HOBt, wherein the contacting is carried out in solution.

9. The method of claim 8, wherein 2-[(tert-butoxy)carbonylamino]-8-bromo-3H-benzo[f]azepin-4-carboxylic acid is prepared by contacting ethyl 2-[(tert-butoxy)carbonylamino]-8-bromo-3H-benzo[b]azepin-4-carboxylate with sodium hydroxide, wherein the contacting is carried out in solution.

10. The method of claim 9, wherein ethyl 2-[(tert-butoxy)carbonylamino]-8-bromo-3H-benzo[b]azepin-4-carboxylate is prepared by contacting (1E,4E)-ethyl-2-amino-8-bromo-3H-benzo[b]azepin-4-carboxylate with di-tert-butyl dicarbonate, wherein the contacting is carried out in solution.

11. The method of claim 10, wherein (1E,4E)-ethyl-2-amino-8-bromo-3H-benzo[b]azepin-4-carboxylate is prepared by contacting (E)-ethyl-3-(4-bromo-2-nitrophenyl)-2-(cyanomethypacrylate with Fe, under conditions effective to cause intramolecular cyclization and formation of (1E,4E)-ethyl-2-amino-8-bromo-3H-benzo[b]azepin-4-carboxylate.

12. The method of claim 11, wherein (E)-ethyl-3-(4-bromo-2-nitrophenyl)-2-(cyanomethyl)acrylate is prepared by contacting 4-bromo-2-nitrobenzaldehyde with ethyl-3-cyano-2-(triphenylphosphanylidine)propanoate, wherein the contacting is carried out in solution and a temperature within the range of about 20° C. to about 25° C.

13. The method of claim 12, wherein ethyl-3-cyano-2-(triphenylphosphanylidine) propanoate is prepared by contacting (carbethoxymethylene)triphenylphosphorane with $BrCH_2CN$, wherein the contacting is carried out in solution.

14. The method of claim 12, wherein 4-bromo-2-nitrobenzaldehyde is prepared by contacting (E)-1-(bromo-2-nitrostyryl)pyrrolidine with $NaIO_4$, wherein the contacting is carried out in solution.

15. The method of claim 14, wherein (E)-1-(bromo-2-nitrostyryl)pyrrolidine is prepared by contacting 4-bromo-2-nitrotoluene with N,N- dimethylformamide dimethylacetal in the presence of dimethylformamide and pyrrolidine.

16. The method of claim 4, wherein the-palladium scavenger is admixed with the solution for a predetermined time; and is then removed to yield the composition of comprising {2-amino-8[4-(pyrrolidinylcarbonyl)phenyl]-(3H-benzo[f] azepin-4-yl)}-N,N-dipropylcarboxamide and one or more palladium-containing contaminants, wherein the palladium is present in a concentration of less than 20 ppm by ICP-OES.

17. The method of claim 16, wherein the predetermined time is about 4 hours or less.

18. The method of claim 16, wherein the palladium scavenger is removed by filtration.

19. The method of claim 5, wherein the contacting is carried out in a solvent comprising ethanol and less than about 0.5% water.

20. The method of claim 4, wherein the method further comprises clarifying the solution of (tert-butoxy)-N-{4-(N, N-dipropylcarbamoyl)-8-[4-(pyrrolidinylcarbonyl)phenyl] (3H-benzo[f]azepin-2-yl}carboxamide by filtration through diatomaceous earth prior to adding the palladium scavenger.

21. The method of claim 20, wherein the palladium scavenger is selected from functionalized silica particles and porous, spherical, non-functional carbon particles, wherein the functionalized silica particles comprise a functional group selected from aminopropyl and mercaptopropyl, and wherein the porous, spherical, non- functional carbon particles have a surface area of about 1200 $m^2$/g, an average pore diameter of about 1 nm, and a particle diameter of about 0.3 mm to about 0.8 mm.

22. The method of claim 19, wherein the method further comprises performing a solvent switch from ethanol to ethyl acetate prior to adding the palladium scavenger.

23. The method of claim 22, wherein the palladium scavenger is selected from functionalized silica particles and functionalized polystyrene particles.

24. The method of claim 19, wherein the contacting is carried out in the presence of a ligand.

25. The method of claim 24, wherein the palladium catalyst is $Pd(OAc)_2$, the ligand is 4,4'-(phenylphosphinidene)bis (benzenesulfonic acid) dipotassium salt hydrate, and wherein the molar ratio of catalyst to ligand is within the range of 1:2 to 1:1.

* * * * *